(12) United States Patent
Kusumi et al.

(10) Patent No.: US 11,471,436 B2
(45) Date of Patent: Oct. 18, 2022

(54) DIHYDRONAPHTHALENE DERIVATIVE

(71) Applicant: ONO PHARMACEUTICAL CO., LTD., Osaka (JP)

(72) Inventors: Kensuke Kusumi, Osaka (JP); Haruto Kurata, Osaka (JP); Atsushi Naganawa, Osaka (JP); Yasuyo Kodera, Osaka (JP); Yuichi Inagaki, Ibaraki (JP); Hiroya Takizawa, Osaka (JP); Mark Allan Wolf, Delanson, NY (US); Joseph Raker, Delmar, NY (US)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 119 days.

(21) Appl. No.: 15/532,389

(22) PCT Filed: Dec. 3, 2015

(86) PCT No.: PCT/JP2015/084019
§ 371 (c)(1),
(2) Date: Jun. 1, 2017

(87) PCT Pub. No.: WO2016/088834
PCT Pub. Date: Jun. 9, 2016

(65) Prior Publication Data
US 2017/0327439 A1 Nov. 16, 2017

Related U.S. Application Data
(60) Provisional application No. 62/087,338, filed on Dec. 4, 2014.

(51) Int. Cl.
| | | |
|---|---|---|
| *A61K 31/397* | (2006.01) | |
| *A61P 25/28* | (2006.01) | |
| *C07D 205/04* | (2006.01) | |
| *C07D 401/10* | (2006.01) | |
| *C07D 207/16* | (2006.01) | |
| *C07D 403/10* | (2006.01) | |
| *A61K 31/015* | (2006.01) | |
| *A61K 31/19* | (2006.01) | |
| *C07C 13/20* | (2006.01) | |
| *C07C 13/48* | (2006.01) | |

(52) U.S. Cl.
CPC .......... *A61K 31/397* (2013.01); *A61K 31/015* (2013.01); *A61K 31/19* (2013.01); *A61P 25/28* (2018.01); *C07C 13/20* (2013.01); *C07C 13/48* (2013.01); *C07D 205/04* (2013.01); *C07D 207/16* (2013.01); *C07D 401/10* (2013.01); *C07D 403/10* (2013.01); *C07C 2602/10* (2017.05)

(58) Field of Classification Search
CPC ............................. A61K 31/397; A61P 25/28
See application file for complete search history.

(56) References Cited

U.S. PATENT DOCUMENTS

| | | |
|---|---|---|
| 2007/0167425 A1 | 7/2007 | Nakade et al. |
| 2009/0275554 A1 | 11/2009 | Habashita et al. |
| 2012/0190649 A1 | 7/2012 | Thomas et al. |

FOREIGN PATENT DOCUMENTS

| | | |
|---|---|---|
| JP | 2013-501074 A | 1/2013 |
| WO | 2005/020882 A2 | 3/2005 |
| WO | 2006/064757 A1 | 6/2006 |
| WO | 2011/017561 A1 | 2/2011 |
| WO | 2012/109108 A1 | 8/2012 |
| WO | 2017/131149 | 8/2017 |

OTHER PUBLICATIONS

Suppliementary Extended European Search Report dated Jul. 27, 2017 by the European Patent Office in counterpart European Patent Application No. 15865945.8.
Itoh, K. et al., "Synthesis and Biological Activities of 3-Aminomethyl-1,2-dihydronaphthalene Derivatives", Chem. Pharm. Bull., 1983, vol. 31, No. 6, pp. 2006-2015.
C. Jaillard, et al., "Edg8/S1P5: An Oligodendroglial Receptor with Dual Function on Process Retraction and Cell Survival", The Journal of Neuroscience, Feb. 9, 2005 • 25(6), pp. 1459-1469.
Alexander S. Novgorodov, et al., "Activation of sphingosine-1-phosphate receptor S1P5 inhibits oligodendrocyte progenitor migration", The FASEB Journal, Research Communication, vol. 21, No. 7 , 2017, total 13 pages.
Thierry Walzer, et al., "Natural killer cell trafficking in vivo requires a dedicated sphingosine 1-phosphate receptor", Nature Immunology, vol. 8, No. 12, Dec. 2007, pp. 1337-1344.
Emilie Debien, et al., "S1PR5 is pivotal for the homeostasis of patrolling monocytes", European Journal of Immunology, Molecular immunology, 2013. 43: pp. 1667-1675.
Richard N. Hanna, et al., "Patrolling monocytes control tumor metastasis to the lung", Science, Nov. 20, 2015 • vol. 350 Issue 6263, total 7 pages.
International Search Report (PCT/ISA/210) dated Feb. 23, 2016 issued by the International Searching Authority in counterpart International Application No. PCT/JP2 015/084019.

(Continued)

*Primary Examiner* — Theodore R. Howell
(74) *Attorney, Agent, or Firm* — Sughrue Mion, PLLC

(57) ABSTRACT

A compound represented by general formula (I) wherein all the symbols are as defined in the specification has a selective S1P5 receptor agonist activity due to having a linker from a phenyl group to a cyclic substituent in a dihydronaphthalene skeleton; i.e., due to having a short linker of one atom or less as L in general formula (I), and can therefore serve as an agent for treating S1P5-mediated disease, e. g., neurodegenerative disease such as schizophrenia.

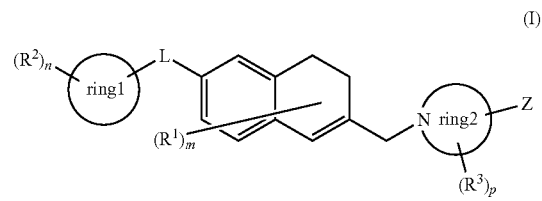

9 Claims, No Drawings

(56) References Cited

OTHER PUBLICATIONS

Written Opinion (PCT/ISA/237) dated Feb. 23, 2016 issued by the International Searching Authority in counterpart International Application No. PCT/JP2 015/084019.
International Searching Authority, International Preliminary Report on Patentability dated Aug. 27, 2020 in copending Application No. PCT/JP2019/006637.

DIHYDRONAPHTHALENE DERIVATIVE

TECHNICAL FIELD

The present invention relates to a compound represented by general formula

[Chemical Formula 1]

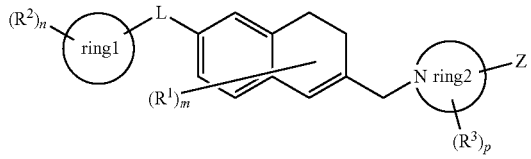

(I)

(wherein, all the symbols have the same meanings as described below), a salt thereof, a solvate thereof, an N-oxide thereof or a prodrug thereof (hereinafter occasionally abbreviated as the compound of the present invention).

BACKGROUND ART

Sphingosine-1-phosphate [(2S,3R,4E)-2-amino-3-hydroxyoctadec-4-enyl-1-phosphate; hereinafter occasionally abbreviated as S1P] is a lipid which is synthesized by metabolic turnover of sphingolipids in cells and by the extracellular action of a secreted sphingosine kinase. It is proposed that sphingosine-1-phosphate acts as an intercellular communication mediator as well as an intracellular second messenger.

Among S1P receptors, with regard to $S1P_5$ (EDG-8) receptor, it is known that $S1P_5$ (EDG-8) receptor is highly expressed in oligodendrocytes (oligodendroglia) and oligodendrocyte progenitor cells. It is revealed that $S1P_5$ receptor promotes the induction of differentiation of oligodendrocyte progenitor cells to oligodendrocytes when $S1P_5$ receptor is activated (see Non Patent Literatures 1 and 2). Oligodendrocytes are a kind of glial cells which form the myelin sheaths (myelin) by binding to the axons of nerve cells. Accordingly, it is considered that a compound which has an agonist activity of $S1P_5$ receptor is useful for treating neurodegenerative disease such as schizophrenia because the compound promotes the regeneration of myelin which has disappeared (demyelination) in nerve cells.

In addition, it is known that $S1P_5$ receptor is highly expressed also in natural killer (NK) cells and it is revealed that the migration of NK cells is induced by the activation of $S1P_5$ receptor (see Non Patent Literature 3).

Further, $S1P_5$ receptor is highly expressed in patrolling monocytes which are known to be involved in the tumor immunity, and therefore, there is a possibility that the activation of the tumor immunity is induced by the activation of $S1P_5$ receptor (see Non Patent Literatures 4 and 5).

Incidentally, as compounds of prior arts to the present invention, the following compounds are known.

As a dihydronaphthalene compound which has binding abilities to S1P receptors, it is disclosed that a compound represented by general formula (a):

[Chemical Formula 2]

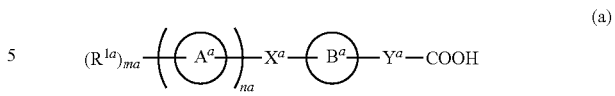

(a)

(wherein, ring $A^a$ represents a cyclic group, ring $B^a$ represents a cyclic group which may further have a substituent(s), $X^a$ represents a bond or a spacer having 1 to 8 atoms in its main chain, $Y^a$ represents a bond or a spacer having 1 to 10 atoms in its main chain, na represents 0 or 1, when na is 0, ma represents 1 and $R^{1a}$ represents a hydrogen atom or a substituent, and when na is 1, ma represents 0 or an integer of 1 to 7 and $R^{1a}$ represents a substituent (in which when ma is 2 or more, a plurality of $R^{1a}$ s may be the same or different) (provided that the definition of each of groups is excerpted)) specifically binds, in particular, to EDG-1 ($S1P_1$) receptor and EDG-6 ($S1P_4$) receptor (see Patent Literature 1).

In addition, as a dihydronaphthalene compound which has binding abilities to S1P receptors, it is disclosed that a compound represented by general formula (b):

[Chemical Formula 3]

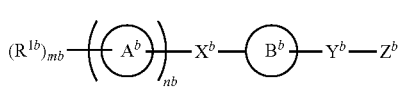

(b)

(wherein, ring $A^b$ represents a cyclic group, ring $B^b$ represents a cyclic group which may further have a substituent(s), $X^b$ represents a bond or a spacer having 1 to 8 atoms in its main chain, $Y^b$ represents a bond or a spacer having 1 to 10 atoms in its main chain, $Z^b$ represents an acidic group which may be protected, nb represents 0 or 1, when nb is 0, mb represents 1 and $R^{1b}$ represents a hydrogen atom or a substituent, and when nb is 1, mb represents 0 or an integer of 1 to 7 and $R^{1b}$ represents a substituent (in which when mb is 2 or more, a plurality of $R^{1b}$s may be the same or different) (provided that the definition of each of groups is excerpted)) binds, in particular, to EDG-1 ($S1P_1$) receptor, EDG-6 ($S1P_4$) receptor and/or EDG-8 ($S1P_5$) receptor (see Patent Literature 2).

Further, as a compound having an S1P agonist activity, a compound represented by general formula (c):

[Chemical Formula 4]

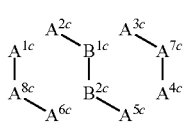

(c)

(wherein, $A^{1c}$ represents $-CX^{1c}=$, $-C(X^{1c})_2-$, $-N=$, $-NX^{1c}-$, $-O-$, $-S-$ or a bond; $A^{2c}$ represents $-CX^{2c}=$, $-C(X^{2c})_2-$, $-N=$, $-NX^{2c}-$, $-O-$ or $-S-$; $A^{3c}$ represents $-CX^{3c}=$, $-C(X^{3c})_2-$, $-N=$, $-NX^{3c}-$, $-O-$, $-S-$ or a bond; $A^{4c}$ represents $-CX^{4c}=$, $-C(X^{4c})_2-$, $-N=$, $-NX^{4c}-$, $-O-$, $-S-$ or a bond; $A^{5c}$ represents $-CX^{5c}=$, $-C(X^{5c})_2-$, $-N=$, $-NX^{5c}-$, $-O-$ or $-S-$; $A^{6c}$ represents $-CX^{6c}=$, $-C(X^{6c})_2-$, $-N=$, $-NX^{6c}-$, $-O-$, $-S-$ or a bond, $A^{7c}$ represents $-C(R^{3c})=$, $-(CR^{3c}R^{fc})-$ or $-NR^{3c}-$;

$A^{8c}$ represents —C(—$W^c$-$Cy^c$)=, —C(—W-$Cy^c$)($R^{fc}$)— or —N(—$W^c$-$Cy^c$)-; $B^{1c}$ represents CH, C or N; $B^{2c}$ represents CH, C or N; $W^c$ represents —C($R^{fc}R^{gc}$)—, —N($R^{fc}$)—, —O—, —S—, —S(O)— or —S(O)$_2$—; $Cy^c$ represents a cycloalkyl group, an aryl group or a heteroaryl group or the like (provided that the definition of each of groups is excerpted)) is known (see Patent Literature 3).

With regard to a compound having a dihydronaphthalene skeleton, none of prior arts disclose nor suggest that the compound of the present invention which is characterized by having a short linker of 1 atom or less as a linker from its phenyl group to its cyclic substituent has improved the balance of an S1P$_5$ receptor agonist activity against an S1P$_1$ receptor agonist activity.

CITATIONS LISTS

Patent Literatures

Patent Literature 1: WO 2005/020882 A
Patent Literature 2: WO 2006/064757 A
Patent Literature 3: WO 2011/017561 A Non Patent Literatures Non Patent Literature 1: The Journal of Neuroscience, Vol. 25, No. 6, pages 1459-1469, 2005
Non Patent Literature 2: The FASEB Journal, Vol. 21, pages 01503-1514, 2007
Non Patent Literature 3: Nature Immunology, Vol. 8, No. 12, pages 1337-1344, 2007
Non Patent Literature 4: European Journal of Immunology, Vol. 43, pages 1667-1675, 2013
Non Patent Literature 5: Science, Vol. 350, No. 6263, pages 985-990, 2015

SUMMARY OF INVENTION

Technical Problems

An object of the present invention is to provide a compound which improves the balance of an S1P$_5$ receptor agonist activity against an S1P$_1$ receptor agonist activity.

Solutions to Problems

The present inventors have carried out intensive studies to find out a compound which improves the balance of an S1P$_5$ receptor agonist activity against an S1P$_1$ receptor agonist activity in order to achieve the above-described object. As a result, the present inventors have found surprisingly that with regard to a compound having a dihydronaphthalene skeleton, the balance of an S1P$_5$ receptor agonist activity against an S1P$_1$ receptor agonist activity is markedly improved by introducing a short linker of 1 atom or less as a linker from its phenyl group to its cyclic substituent, and have completed the present invention.

In other words, the present invention relates to the followings:

[1] a compound represented by general formula (I):

[Chemical Formula 5]

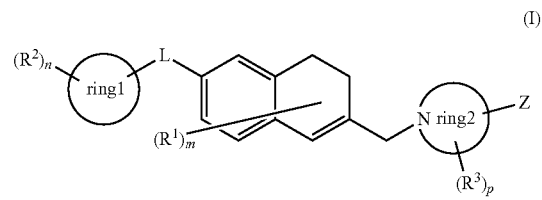

[wherein, $R^1$ represents a C1-4 alkyl group, a halogen atom, a C1-4 haloalkyl group or a C1-4 alkoxy group;

$R^2$ represents a C1-4 alkyl group, a halogen atom, a C1-4 haloalkyl group or an SF$_5$ group;

$R^3$ represents a C1-4 alkyl group;

L represents a bond, —CH$_2$— or —O—;

Z represents an acidic group which may be substituted with a C1-8 alkyl group;

ring 1 represents a 3- to 10-membered cyclic group;

ring 2 represents a 3- to 7-membered nitrogen-containing heterocyclic ring;

m represents an integer of 0 to 6;

n represents an integer of 0 to 5;

p represents an integer of 0 to 5;

when m is 2 or more, a plurality of $R^1$s may be the same or different;

when n is 2 or more, a plurality of $R^2$s may be the same or different; and when p is 2 or more, a plurality of $R^3$s may be the same or different];

(provided that 1-{[6-(4-butylphenoxy)-1-methyl-3,4-dihydronaphthalen-2-yl]methyl}azetidine-3-carboxylic acid is excluded);

a salt thereof, a solvate thereof, an N-oxide thereof or a prodrug thereof;

[2] the compound according to the above [1], wherein Z is (1) a carboxyl group which may be substituted with a C1-8 alkyl group, (2) a hydroxy group which may be substituted with a C1-8 alkyl group, (3) a hydroxamic acid group which may be substituted with a C1-8 alkyl group, (4) a sulfonic acid group which may be substituted with a C1-8 alkyl group, (5) a boronic acid group which may be substituted with a C1-8 alkyl group, (6) a carbamoyl group which may be substituted with a C1-8 alkyl group, (7) a sulfamoyl group which may be substituted with a C1-8 alkyl group, (8) a sulfoximine group which may be substituted with a C1-8 alkyl group or (9) a tetrazolyl group;

[3] the compound according to the above [1] or [2], wherein Z is a carboxyl group which may be substituted with a C1-8 alkyl group;

[4] the compound according to any one of the above [1] to [3], wherein ring 1 is a 5- to 7-membered cyclic group;

[5] the compound according to any one of the above [1] to [3], wherein ring 1 is (1) cyclopentane, (2) cyclohexane, (3) cycloheptane, (4) cyclopentene, (5) benzene, (6) pyridine, (7) naphthalene, (8) indole or (9) dihydroindole;

[6] the compound according to any one of the above [1] to [3], wherein m is an integer of 1 or 2;

[7] the compound according to the above [1], which is a compound represented by general formula (I-1):

[Chemical Formula 6]

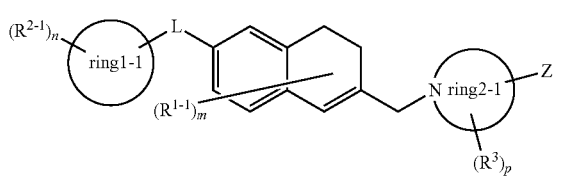

(I-1)

[wherein, $R^{1-1}$ represents a C1-4 alkyl group or a halogen atom, $R^{2-1}$ represents a C1-3 alkyl group, a halogen atom or a C1-3 haloalkyl group, ring 1-1 represents a 5- to 7-membered cyclic group, ring 2-1 represents a 4- to 7-membered nitrogen-containing saturated heterocyclic ring, m-1 represents an integer of 1 or 2, when m-1 is 2, a plurality of $R^{1-1}$s may be the same or different, when n is 2 or more, a plurality of $R^{2-1}$s may be the same or different and other symbols have the same meanings as described in the above [1]];

[8] the compound according to the above [1], which is (1) 1-{[6-(cyclohexyloxy)-3,4-dihydro-2-naphthalenyl]methyl}-3-azetidinecarboxylic acid, (2) 1-{[6-(cyclohexyloxy)-3-methyl-3,4-dihydro-2-naphthalenyl]methyl}-3-azetidinecarboxylic acid, (3) 1-{[1-methyl-6-(2-pyridinyl)-3,4-dihydro-2-naphthalenyl]methyl}-3-azetidinecarboxylic acid, (4) 1-[(1-methyl-6-phenyl-3,4-dihydro-2-naphthalenyl)methyl]-3-azetidinecarboxylic acid or (5) 1-{[6-(4-fluorophenoxy)-1-methyl-3,4-dihydro-2-naphthalenyl]methyl}-3-azetidinecarboxylic acid;

[9] a pharmaceutical composition comprising the compound represented by general formula (I) according to the above [1], a salt thereof, a solvate thereof, an N-oxide thereof or a prodrug thereof;

[10] the pharmaceutical composition according to the above [9], which is an $S1P_5$ agonist;

[11] the pharmaceutical composition according to the above [9], which is an agent for preventing and/or treating $S1P_5$-mediated disease;

[12] the pharmaceutical composition according to the above [11], wherein the $S1P_5$-mediated disease is neurodegenerative disease, autoimmune disease, infection or cancer;

[13] the pharmaceutical composition according to the above [12], wherein the neurodegenerative disease is schizophrenia, Binswanger's disease, multiple sclerosis, neuromyelitis optica, Alzheimer's disease, cognitive impairment, amyotrophic lateral sclerosis or spinocerebellar ataxia;

[14] a method for preventing and/or treating $S1P_5$-mediated disease, comprising administering to a mammal an effective amount of the compound represented by general formula (I) according to the above [1], a salt thereof, a solvate thereof, an N-oxide thereof or a prodrug thereof;

[15] the compound represented by general formula (I) according to the above [1], a salt thereof, a solvate thereof, an N-oxide thereof or a prodrug thereof for preventing and/or treating $S1P_5$-mediated disease;

[16] use of the compound represented by general formula (I) according to the above [1], a salt thereof, a solvate thereof, an N-oxide thereof or a prodrug thereof for manufacture of an agent for preventing and/or treating $S1P_5$-mediated disease; and the like.

Advantageous Effects of Invention

The compound of the present invention has a highly selective $S1P_5$ receptor agonist activity than $S1P_1$ receptor agonist activity, and therefore, the compound of the present invention is useful for treating $S1P_5$-mediated disease, for example, neurodegenerative disease, autoimmune disease, infection and cancer.

DESCRIPTION OF EMBODIMENTS

The present invention will be described in details hereinbelow.

In the present invention, the phrase "to improve the balance of an $S1P_5$ receptor agonist activity against an $S1P_1$ receptor agonist activity" means "to increase the selectivity of an $S1P_5$ receptor agonist activity against an $S1P_1$ receptor agonist activity".

In the present invention, a halogen atom means fluorine, chlorine, bromine or iodine.

In the present invention, a C1-8 alkyl group includes a linear or branched C1-8 alkyl group. Examples of the C1-8 alkyl group include methyl, ethyl, propyl, butyl, pentyl, hexyl, heptyl, octyl, isopropyl, isobutyl, sec-butyl, tert-butyl, 1-methylbutyl, 1-ethylpropyl, 1,1-dimethylpropyl, 1,2-dimethylpropyl, 2-methylbutyl, 3-methylbutyl, 2,2-dimethylpropyl, 1-methylpentyl, 1-ethylbutyl, 2-ethylbutyl, 1-ethyl-1-methylpropyl, 1-ethyl-2-methylpropyl, 1,1-dimethylbutyl, 1,2-dimethylbutyl, 1,3-dimethylbutyl, 2-methylpentyl, 3-methylpentyl, 4-methylpentyl, 2,3-dimethylbutyl, 1-methylhexyl, 1-ethylpentyl, 2-ethylpentyl, 1-propylbutyl, 2-methyl-3-hexyl, 1,2-dimethylpentyl, 1,3-dimethylpentyl, 1,4-dimethylpentyl, 1-ethyl-1-methylbutyl, 1-methyl-2-ethylbutyl, 1-ethyl-2-methylbutyl, 1-ethyl-3-methylbutyl, 1,1-dimethylpentyl, 1,1,3-trimethylbutyl, 1,1-diethylpropyl, 2-methylhexyl, 3-methylhexyl, 4-methylhexyl, 5-methylhexyl, 3-ethylpentyl, 1-methylheptyl, 2-methylheptyl, 3-methylheptyl, 4-methylheptyl, 5-methylheptyl, 6-methylheptyl, 1-ethylhexyl, 2-ethylhexyl, 3-ethylhexyl, 1-propylpentyl, 2-propylpentyl, 1,5-dimethylhexyl, 1-ethyl-4-methylpentyl, 1-propyl-3-methylbutyl, 1,1-dimethylhexyl, 1-ethyl-1-methylpentyl and 1,1-diethylbutyl groups.

In the present invention, a C1-4 alkyl group includes a linear or branched C1-4 alkyl group. Examples of the C1-4 alkyl group include methyl, ethyl, propyl, butyl, isopropyl, isobutyl, sec-butyl and tert-butyl groups.

In the present invention, a C1-3 alkyl group includes a linear or branched C1-3 alkyl group. Examples of the C1-3 alkyl group include methyl, ethyl, propyl and isopropyl groups.

In the present invention, a C1-4 haloalkyl group means a fluoromethyl group, a chloromethyl group, a bromomethyl group, a iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group, a 3-chloropropyl group, a 4,4,4-trifluorobutyl group or a 4-bromobutyl group.

In the present invention, a C1-3 haloalkyl group means a fluoromethyl group, a chloromethyl group, a bromomethyl group, a iodomethyl group, a difluoromethyl group, a trifluoromethyl group, a 1-fluoroethyl group, a 2-fluoroethyl group, a 2-chloroethyl group, a pentafluoroethyl group, a 1-fluoropropyl group, a 2-chloropropyl group, a 3-fluoropropyl group or a 3-chloropropyl group.

In the present invention, examples of a C1-4 alkoxy group include methoxy, ethoxy, propoxy, isopropoxy, butoxy, isobutoxy, sec-butoxy and tert-butoxy groups.

In the present invention, examples of an acidic group include a carboxyl group, a hydroxy group, a hydroxamic acid group, a sulfonic acid group, a boronic acid group, a carbamoyl group, a sulfamoyl group, a sulfoximine group (—SH(=O)(=NH)) and a tetrazolyl group.

In the present invention, a 3- to 10-membered cyclic group means a C3-10 carbocyclic ring or a 3- to 10-membered heterocyclic ring.

In the present invention, a C3-10 carbocyclic ring refers to a carbocyclic ring which is a C3-10 monocyclic or bicyclic carbocyclic ring and which may be partially or wholly saturated. Examples of the C3-10 carbocyclic ring include cyclopropane, cyclobutane, cyclopentane, cyclohexane, cycloheptane, cyclooctane, cyclononane, cyclodecane, cyclopentene, cyclohexene, cycloheptene, cyclooctene, cyclopentadiene, cyclohexadiene, cycloheptadiene, cyclooctadiene, benzene, pentalene, perhydropentalene, azulene, perhydroazulene, indene, perhydroindene, indane, naphthalene, dihydronaphthalene, tetrahydronaphthalene and perhydronaphthalene.

In the present invention, a 3- to 10-membered heterocyclic ring refers to a partially or wholly saturated 3- to 10-membered monocyclic or bicyclic heterocyclic ring which contains 1 to 5 heteroatoms selected from an oxygen atom, a nitrogen atom and a sulfur atom. Examples of the 3- to 10-membered heterocyclic ring include pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine, thiadiazepine, indole, isoindole, indolizine, benzofuran, isobenzofuran, benzothiophene, isobenzothiophene, dithianaphthalene, indazole, quinoline, isoquinoline, quinolizine, purine, phthalazine, pteridine, naphthyridine, quinoxaline, quinazoline, cinnoline, benzoxazole, benzothiazole, benzimidazole, chromene, benzofurazan, benzothiadiazole, benzotriazole, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, oxirane, oxetane, dihydrofuran, tetrahydrofuran, dihydropyran, tetrahydropyran, dihydrooxepin, tetrahydrooxepin, perhydrooxepin, thiirane, thietane, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, perhydrothiadiazepine, tetrahydrothiadiazepine, perhydrothiadiazepine, morpholine, thiomorpholine, oxathiane, indoline, isoindoline, dihydrobenzofuran, perhydrobenzofuran, dihydroisobenzofuran, perhydroisobenzofuran, dihydrobenzothiophene, perhydrobenzothiophene, dihydroisobenzothiophene, perhydroisobenzothiophene, dihydroindazole, perhydroindazole, dihydroquinoline, tetrahydroquinoline, perhydroquinoline, dihydroisoquinoline, tetrahydroisoquinoline, perhydroisoquinoline, dihydrophthalazine, tetrahydrophthalazine, perhydrophthalazine, dihydronaphthyridine, tetrahydronaphthyridine, perhydronaphthyridine, dihydroquinoxaline, tetrahydroquinoxaline, perhydroquinoxaline, dihydroquinazoline, tetrahydroquinazoline, perhydroquinazoline, dihydrocinnoline, tetrahydrocinnoline, perhydrocinnoline, benzoxathiane, dihydrobenzoxazine, dihydrobenzothiazine, pyrazinomorpholine, dihydrobenzoxazole, perhydrobenzoxazole, dihydrobenzothiazole, perhydrobenzothiazole, dihydrobenzimidazole, perhydrobenzimidazole, dioxolane, dioxane, dithiolane, dithiane, dioxaindane, benzodioxane, chromane, benzodithiolane and benzodithiane rings.

In the present invention, a 5- to 7-membered cyclic group means a C5-7 carbocyclic ring or a 5- to 7-membered heterocyclic ring.

In the present invention, a C5-7 carbocyclic ring means a C5-7 monocyclic carbocyclic ring which may be partially or wholly saturated. Examples of the C5-7 carbocyclic ring include cyclopentane, cyclohexane, cycloheptane, cyclopentene, cyclohexene, cycloheptene, cyclopentadiene, cyclohexadiene, cycloheptadiene and benzene rings.

In the present invention, a 5- to 7-membered heterocyclic ring includes a 5- to 7-membered unsaturated heterocyclic ring and a 5- to 7-membered saturated heterocyclic ring. Examples of the 5- to 7-membered heterocyclic ring include pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrofuran, tetrahydrofuran, dihydropyran, tetrahydropyran, dihydrooxepin, tetrahydrooxepin, perhydrooxepin, dihydrothiophene, tetrahydrothiophene, dihydrothiopyran, tetrahydrothiopyran, dihydrothiepine, tetrahydrothiepine, perhydrothiepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine, oxathiane, dioxolane, dioxane, dithiolane, dithiane, pyrrole, imidazole, triazole, tetrazole, pyrazole, pyridine, pyrazine, pyrimidine, pyridazine, azepine, diazepine, furan, pyran, oxepin, thiophene, thiopyran, thiepine, oxazole, isoxazole, thiazole, isothiazole, furazan, oxadiazole, oxazine, oxadiazine, oxazepine, oxadiazepine, thiadiazole, thiazine, thiadiazine, thiazepine and thiadiazepine rings.

In the present invention, a 3- to 7-membered nitrogen-containing heterocyclic ring refers to an unsaturated or saturated 3- to 7-membered monocyclic heterocyclic ring which contains 1 to 5 heteroatoms selected from an oxygen atom, a nitrogen atom and a sulfur atom and which essentially contains one or more nitrogen atoms. Examples of the 3- to 7-membered nitrogen-containing heterocyclic ring include pyrrole, imidazole, triazole, tetrazole, pyrazole, pyridine, pyrazine, pyrimidine, pyridazine, azepine, diazepine, oxazepine, oxadiazepine, thiazepine, thiadiazepine, oxazole, isoxazole, thiazole, isothiazole, furazan, oxadiazole, oxazine, oxadiazine, thiadiazole, thiazine, thiadiazine, aziridine, azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, dihydroazepine, tetrahydroazepine, perhydroazepine, dihydrodiazepine, tetrahydrodiazepine, perhydrodiazepine, dihydrooxazepine, tetrahydrooxazepine, perhydrooxazepine, dihydrooxadiazepine, tetrahydrooxadiazepine, perhydrooxadiazepine, dihydrothiazepine, tetrahydrothiazepine, perhydrothiazepine, dihydrothiadiazepine, tetrahydrothiadiazepine and perhydrothiadiazepine rings.

In the present invention, a 4- to 7-membered nitrogen-containing saturated heterocyclic ring refers to a partially or wholly saturated 4- to 7-membered monocyclic heterocyclic ring which contains 1 to 5 heteroatoms selected from an oxygen atom, a nitrogen atom and a sulfur atom and which essentially contains one or more nitrogen atoms. Examples of the 4- to 7-membered nitrogen-containing saturated heterocyclic ring include azetidine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydroazepine, tetrahydroazepine, perhydroazepine, dihydrodiazepine, tetrahydrodiazepine, perhydrodiazepine, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrooxazepine, tetrahydrooxazepine, perhydrooxazepine, dihydrooxadiazepine, tetrahydrooxadiazepine, perhydrooxadiazepine, dihydrothiadiazole, tetrahydrothiadiazole (thiadiazolidine), dihydrothiazine, tetrahydrothiazine, dihydrothiadiazine, tetrahydrothiadiazine, dihydrothiazepine, tetrahydrothiazepine, perhydrothiazepine, dihydrothiadiazepine, tetrahydrothiadiazepine, perhydrothiadiazepine, morpholine, thiomorpholine and the like.

In the present invention, $R^1$ is preferably a C1-4 alkyl group or a halogen atom, is more preferably a C1-4 group and is particularly preferably a methyl group.

In the present invention, $R^2$ is preferably a C1-3 alkyl group, a halogen atom or a C1-3 haloalkyl group.

In the present invention, Z is preferably a carboxyl group which may be substituted with a C1-8 alkyl group.

In the present invention, ring 1 is preferably a 5- to 7-membered cyclic group.

In the present invention, ring 1 is preferably cyclopentane, cyclohexane, cycloheptane, cyclopentene, benzene, pyridine, naphthalene, indole or dihydroindole.

In the present invention, ring 2 is preferably a 4- to 7-membered nitrogen-containing saturated heterocyclic ring and is more preferably azetidine, pyrrolidine, piperidine or perhydroazepine.

In the present invention, a compound represented by general formula (I-1):

[Chemical Formula 7]

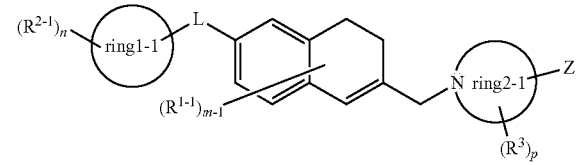

(I-1)

[wherein, $R^{1-1}$ represents a C1-4 alkyl group or a halogen atom, $R^{2-1}$ represents a C1-3 alkyl group, a halogen atom or a C1-3 haloalkyl group, ring 1-1 represents a 5- to 7-membered cyclic group, ring 2-1 represents a 4- to 7-membered nitrogen-containing saturated heterocyclic ring, m-1 represents an integer of 1 or 2 and other symbols have the same meanings as described above] is more preferable.

In the present invention, in general formula (I-1), $R^{1-1}$ is preferably a C1-4 alkyl group and is more preferably a methyl group.

In the present invention, in general formula (I-1), a 5- to 7-membered cyclic group represented by ring 1-1 is preferably cyclopentane, cyclohexane, cycloheptane, cyclopentene, benzene or pyridine.

As another aspect of the present invention, in general formula (I-1), ring 1-1 may be cyclopentane, cyclohexane, cycloheptane, cyclopentene, benzene, pyridine, naphthalene, indole or dihydroindole.

In the present invention, in general formula (I-1), a 4- to 7-membered nitrogen-containing saturated heterocyclic ring represented by ring 2-1 is preferably azetidine, pyrrolidine, piperidine or perhydroazepine.

In the present invention, compounds described in Examples are more preferable and (1)
1-{[6-(cyclohexyloxy)-3,4-dihydro-2-naphthalenyl]methyl}-3-azetidinecarboxylic acid, (2)
1-{[6-(cyclohexyloxy)-3-methyl-3,4-dihydro-2-naphthalenyl]methyl}-3-azetidinecarboxylic acid, (3)
1-{[1-methyl-6-(2-pyridinyl)-3,4-dihydro-2-naphthalenyl]methyl}-3-azetidinecarboxylic acid, (4)
1-[(1-methyl-6-phenyl-3,4-dihydro-2-naphthalenyl)methyl]-3-azetidinecarboxylic acid or (5)

1-{[6-(4-fluorophenoxy)-1-methyl-3,4-dihydro-2-naphthalenyl]methyl}-3-azetidinecarboxylic acid is even more preferable.

[Isomers]

Unless otherwise specifically indicated, all isomers are included in the present invention. For example, an alkyl group includes linear and branched ones. In addition, all of geometric isomers due to double bond(s), ring(s) and fused ring(s) ((E)-, (Z)-, cis- and trans-forms), optical isomers due to the presence of asymmetric carbon atom(s) and the like (R-, S-, α- and, β-configurations, enantiomer(s) and diastereomer(s)), optically active substances having optical rotation (D-, L-, d- and l-forms), polar substances by chromatographic separation (more polar and less polar substances), compounds in equilibrium, rotational isomers, a mixture thereof in any proportion and a racemic mixture are included in the present invention. In addition, tautomers are all included in the present invention.

Further, optical isomers in the present invention may include, not only 100%-pure isomers, but also less than 50%-pure optical isomers.

In the present invention, unless otherwise specified, the symbol:
[Chemical Formula 8]

represents that a substituent binds to the back side on the paper surface (in other words, α-configuration), the symbol:
[Chemical Formula 9]

represents that a substituent binds to the front side on the paper surface (in other words, β-configuration), and the symbol:
[Chemical Formula 10]

represents α-configuration, β-configuration or a mixture thereof at an appropriate ratio, as would be apparent to those skilled in the art.

The compound represented by general formula (I) can be converted into a corresponding salt by a known method. The salt is preferably a water-soluble salt. In addition, the salt is preferably a pharmaceutically acceptable salt. Examples of the appropriate salt include a salt of an alkali metal (such as potassium and sodium), a salt of an alkaline earth metal (such as calcium and magnesium), an ammonium salt, a salt of a pharmaceutically acceptable organic amine (such as tetramethylammonium, triethylamine, methylamine, dimethylamine, cyclopentylamine, benzylamine, phenethylamine, piperidine, monoethanolamine, diethanolamine, tris(hydroxymethyl)aminomethane, lysine, arginine and N-methyl-D-glucamine) as well as an acid addition salt (such as a salt of an inorganic acid (such as a hydrochloride, a hydrobromide, a hydroiodide, a sulfate, a phosphate and a nitrate) and a salt of an organic acid (such as an acetate, a trifluoroacetate, a lactate, a tartrate, an oxalate, a fumarate, a maleate, a benzoate, a citrate, a methanesulfonate, an ethanesulfonate, a benzenesulfonate, a toluenesulfonate, an isethionate, a glucuronate and a gluconate)) and the like.

The compound represented by general formula (I) or a salt thereof can be also converted into a solvate. The solvate is preferably a low-toxicity and water-soluble solvate. Examples of the appropriate solvate include a solvate of water and a solvate of an alcohol based solvent (such as a solvate of ethanol).

An N-oxide of the compound represented by general formula (I) represents a compound obtained by oxidation a nitrogen atom in the compound represented by general formula (I). In addition, the N-oxide of the compound represented by general formula (I) may be further converted to the above-described alkali (alkaline earth) metal salt, the ammonium salt, the organic amine salt or the acid addition salt.

In addition, a prodrug of the compound represented by general formula (I) refers to a compound which is converted to the compound represented by general formula (I) by a reaction with an enzyme, gastric acid and the like in vivo. Examples of the prodrug of the compound represented by general formula (I) include the followings: when the compound represented by general formula (I) has a hydroxy group, a compound obtained by making the hydroxy group in the compound represented by general formula (I) is acylated, alkylated, phosphorylated or borated (for example, a compound obtained by making the hydroxy group in the compound of the present invention is acetylated, palmitoylated, propanoylated, pivaloylated, succinylated, fumarylated, alanylated, dimethylaminomethylcarbonylated or the like); a compound obtained by making a carboxyl group in the compound represented by general formula (I) is esterified or amidated (for example, a compound obtained by making a carboxyl group in the compound represented by general formula (I) is an ethyl ester, an isopropyl ester, a phenyl ester, a carboxymethyl ester, a dimethylaminomethyl ester, a pivaloyloxymethyl ester, an ethoxycarbonyloxyethyl ester, a phthalidyl ester, a (5-methyl-2-oxo-1,3-dioxolen-4-yl)methyl ester, a cyclohexyloxycarbonylethyl ester, a methylamide or the like); and the like. These compounds can be prepared by a known method. In addition, the prodrug of the compound represented by general formula (I) may be either a hydrate or a non-hydrate. Further, the prodrug of the compound represented by general formula (I) may be a compound which is converted to the compound represented by general formula (I) under a physiological condition as described in "*Iyakuhin no kaihatsu*", Vol. 7, "*Bunshi sekkei*", pages 163-198, Hirokawa-Shoten Ltd., published 1990. Furthermore, the compound represented by general formula (I) may also be labeled by an isotope (for example, $^2$H, $^3$H, $^{11}$C, $^{13}$C, $^{14}$C, $^{13}$N, $^{15}$N, $^{15}$O, $^{17}$O, $^{18}$O, $^{35}$S, $^{18}$F, $^{36}$Cl, $^{123}$I, $^{125}$I and the like) and the like.

[Processes for the Preparation of the Compound of the Present Invention]

The compound of the present invention can be prepared by a known method. For example, the compound of the present invention can be prepared by appropriately improving a method described in Comprehensive Organic Transformations: A Guide to Functional Group Preparations, 2nd Edition (Richard C. Larock, John Wiley & Sons Inc., 1999) or the methods described in Examples and the like or combining these methods.

In general formula (I), a compound in which L is an oxygen atom and ring 2 is a 4- to 7-membered nitrogen-containing saturated heterocyclic ring, i.e., a compound represented by general formula (I-A):

[Chemical Formula 11]

(I-A)

(wherein, ring $2^A$ represents a 4- to 7-membered nitrogen-containing saturated heterocyclic ring and all the symbols represent the same meanings as described above) can be prepared by Reaction Scheme 1 shown below.

Reaction Scheme 1

[Chemical Formula 12]

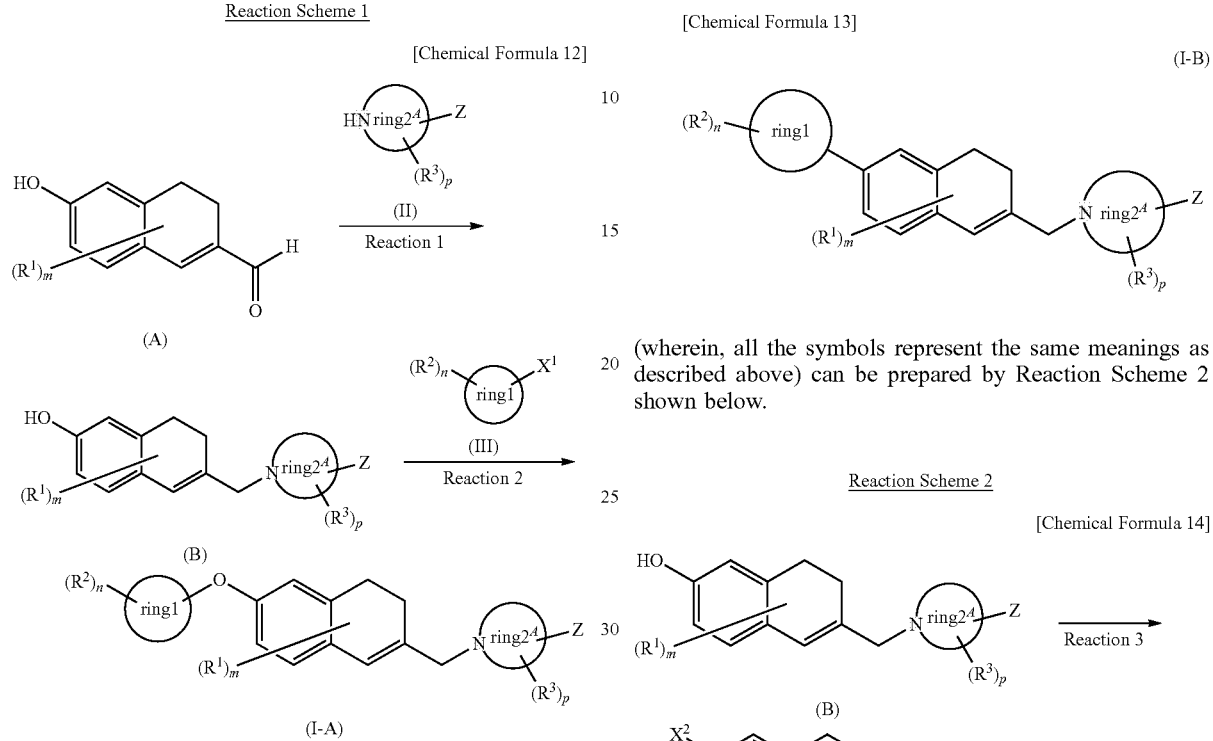

(wherein, $X^1$ represents a halogen atom, a trifluoromethanesulfonyloxy group (an OTf group) or a methanesulfonyloxy group (an OMs group) and other symbols have the same meanings as described above).

In Reaction Scheme 1, Reaction 1 can be performed by subjecting a compound represented by general formula (A) and a compound represented by general formula (II) to a reductive amination reaction. The reductive amination reaction is known, and for example, is performed in an organic solvent (such as dichloroethane, dichloromethane, N,N-dimethylformamide, N,N-dimethylacetamide, N-methylpyrrolidone, acetic acid, tetrahydrofuran, methanol and a mixture thereof) in the presence of a reducing agent (such as sodium triacetoxyborohydride, sodium cyanoborohydride and sodium borohydride) at a temperature of 0 to 40° C.

In Reaction Scheme 1, Reaction 2 can be performed by subjecting a compound represented by general formula (B) and a compound represented by general formula (III) to an etherification reaction. The etherification reaction is known, and for example, is performed by a reaction in an organic solvent (such as N,N-dimethylacetamide, N,N-dimethylformamide, N-methylpyrrolidone, dimethyl sulfoxide, chloroform, dichloromethane, diethyl ether, tetrahydrofuran and methyl t-butyl ether) in the presence of a hydroxide of an alkali metal (such as sodium hydroxide, potassium hydroxide and lithium hydroxide), a hydride of an alkali metal (such as sodium hydride), a hydroxide of an alkaline earth metal (such as barium hydroxide and calcium hydroxide), a phosphate (such as potassium phosphate), a carbonate (such as cesium carbonate, sodium carbonate and potassium carbonate), an aqueous solution thereof or a mixture thereof at 0 to 100° C.

In general formula (I), a compound in which L is a bond and ring 2 is a 4- to 7-membered nitrogen-containing saturated heterocyclic ring, i.e., a compound represented by general formula (I-B):

[Chemical Formula 13]

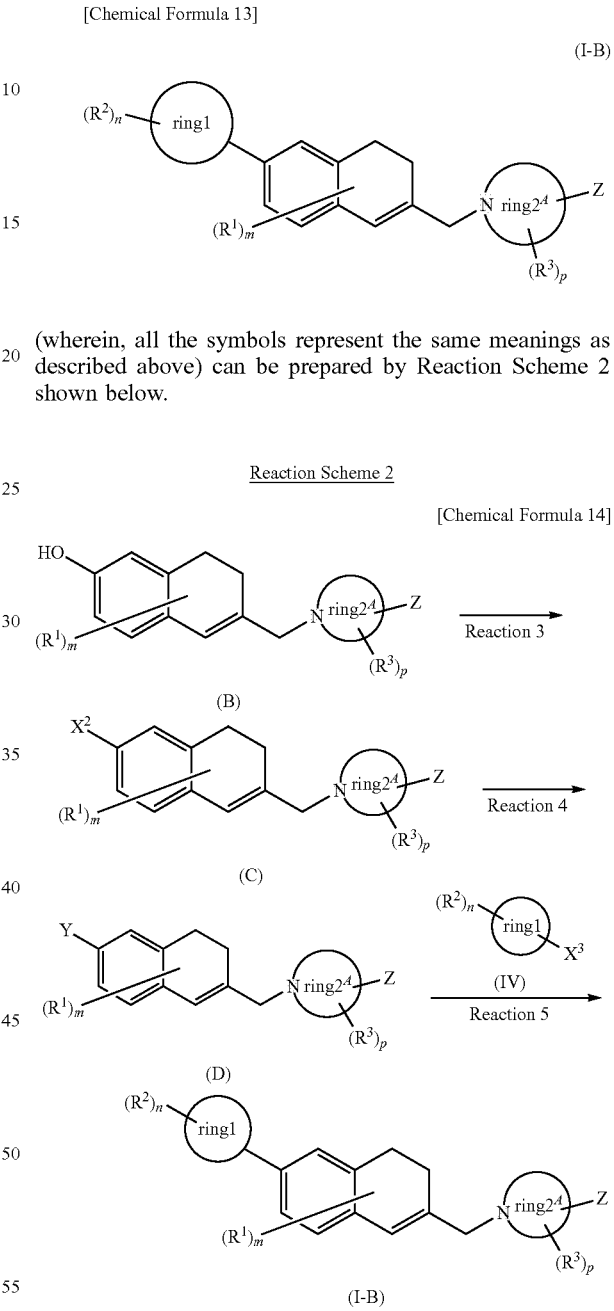

(wherein, all the symbols represent the same meanings as described above) can be prepared by Reaction Scheme 2 shown below.

(wherein, $X^2$ represents a trifluoromethanesulfonyloxy group (an OTf group), Y represents a boronic acid group (—B(OH)$_2$) or a boronate ester group (—B(ORi)(ORii) (wherein, Ri and Rii represent a C1-3 alkyl group and Ri and Rii may take together to form a ring), for example, 4,4,5,5-tetramethyl-1,3,2-dioxaborolan-2-yl and the like), $X^3$ represents a halogen atom and other symbols have the same meanings as described above).

In Reaction Scheme 2, Reaction 3 is known, and is performed by using a compound represented by general formula (B), for example, in an organic solvent (such as dichloromethane, chloroform, dichloroethane, pyridine, triethylamine and a mixture thereof), in the presence of a base (such as triethylamine, pyridine and N-ethyl N,N-diisopropylamine) and a trifluoromethylating reagent (such as trifluoromethanesulfonic anhydride, trifluoromethanesulfonyl chloride and N,N-bis(trifluoromethylsulfonyl)aniline) at a temperature of −80 to 40° C.

In Reaction Scheme 2, Reaction 4 is known and is performed by using a compound represented by general formula (C), for example, in an organic solvent (such as 1,4-dioxane, dimethyl sulfoxide, dimethylformamide, dimethylacetamide, N-methylpyrrolidone, dichloromethane, dichloroethane and tetrahydrofuran) in the presence of a palladium catalyst (such as tetrakis(triphenylphosphine)palladium ($Pd(PPh_3)_4$), dichlorobis(triphenylphosphine)palladium ($Cl_2\ Pd(PPh_3)_2$), palladium acetate ($Pd(OAc)_2$), 1,1'-bis(diphenylphosphino)ferrocene palladium (II) dichloride dichloromethane complex ($PdCl_2(dppf)$-$CH_2Cl_2$)), a boric acid reagent (such as bis(pinacolato)diborone and pinacolborone), and as necessary, in the presence of a base (such as triethylamine, pyridine, N-ethyl N,N-diisopropylamine, potassium carbonate, sodium carbonate, cesium carbonate and potassium phosphate) or a fluorination reagent (such as potassium fluoride), at a temperature of room temperature to 100° C.

In Reaction Scheme 2, Reaction 5 is known, and can be prepared by subjecting a compound represented by general formula (D) and a compound represented by general formula (IV) to a Suzuki coupling reaction. The reaction is known, and for example, can be performed in an organic solvent (such as toluene, benzene, N,N-dimethylformamide (DMF), tetrahydrofuran, methanol, ethanol, acetonitrile, dimethoxyethane, acetone, dioxane and dimethylacetamide) and water in the presence of a palladium catalyst (such as tetrakis(triphenylphosphine)palladium ($Pd(PPh_3)_4$), dichlorobis(triphenylphosphine)palladium ($Cl_2\ Pd(PPh_3)_2$), palladium acetate ($Pd(OAc)_2$) and bis(tri-tert-butylphosphine)palladium (0) ($Pd(tBu_3P)_2$)) in the presence of a base (such as sodium ethylate, sodium hydroxide, potassium hydroxide, triethylamine, sodium carbonate, sodium bicarbonate, potassium carbonate, cesium carbonate, thallium carbonate, tripotassium phosphate, cesium fluoride, barium hydroxide and tetrabutylammonium fluoride) at room temperature to 120° C.

In Reaction Schemes 1 and 2, when a protecting group is present in each of the compounds represented by general formulae, for example, when Z is protected, a deprotection reaction can be performed, as necessary. The deprotection reaction of the protecting group is known and can be performed by the following methods. Examples of the deprotection reaction include (1) a deprotection reaction by alkaline hydrolysis, (2) a deprotection reaction under an acidic condition, (3) a deprotection reaction by hydrogenolysis, (4) a deprotection reaction of a silyl group, (5) a deprotection reaction by using a metal, (6) a deprotection reaction by using a metal complex and the like.

These methods are described specifically as follows.

(1) A deprotection reaction by alkaline hydrolysis is performed, for example, in an organic solvent (such as methanol, tetrahydrofuran and dioxane), by using a hydroxide of an alkali metal (such as sodium hydroxide, potassium hydroxide and lithium hydroxide), a hydroxide of an alkaline earth metal (such as barium hydroxide and calcium hydroxide), a carbonate (such as sodium carbonate and potassium carbonate), an aqueous solution thereof or a mixture thereof at 0 to 40° C.

(2) A deprotection reaction under an acidic condition is performed, for example, in an organic solvent (such as dichloromethane, chloroform, dioxane, ethyl acetate, methanol, isopropyl alcohol, tetrahydrofuran and anisole), in an organic acid (such as acetic acid, trifluoroacetic acid, methanesulfonic acid and p-tosylic acid), an inorganic acid (such as hydrochloric acid and sulfuric acid) or a mixture thereof (such as hydrobromic acid/acetic acid) in the presence or absence of 2,2,2-trifluoroethanol at 0 to 100° C.

(3) A deprotection reaction by hydrogenolysis is performed, for example, in a solvent (such as an ether-based solvent (such as tetrahydrofuran, dioxane, dimethoxyethane and diethyl ether), an alcohol-based solvent (such as methanol and ethanol), a benzene-based solvent (such as benzene and toluene), a ketone-based solvent (such as acetone and methyl ethyl ketone), a nitrile-based solvent (such as acetonitrile), an amide-based solvent (such as N,N-dimethylformamide), water, ethyl acetate, acetic acid or a mixed solvent of two or more of them), in the presence of a catalyst (such as a palladium-carbon, a palladium black, palladium hydroxide-carbon, platinum oxide and a Raney nickel), under hydrogen atmosphere at a normal pressure or under pressurization or in the presence of ammonium formate, at 0 to 200° C.

(4) A deprotection reaction of a silyl group is performed, for example, in a water-miscible organic solvent (such as tetrahydrofuran and acetonitrile), by using tetrabutylammonium fluoride at 0 to 40° C. In addition, a deprotection reaction of a silyl group is performed, for example, in an organic acid (such as acetic acid, trifluoroacetic acid, methanesulfonic acid and p-tosylic acid), an inorganic acid (such as hydrochloric acid and sulfuric acid) or a mixture thereof (such as hydrobromic acid/acetic acid) at −10 to 100° C.

(5) A deprotection reaction by using a metal is performed, for example, in an acidic solvent (such as acetic acid, a buffer solution of pH 4.2 to 7.2 or a mixed solution of such a solution and an organic solvent such as tetrahydrofuran), in the presence of powdery zinc, if necessary, while applying an ultrasonic wave, at 0 to 40° C.

(6) A deprotection reaction by using a metal complex is performed, for example, in an organic solvent (such as dichloromethane, N,N-dimethylformamide, tetrahydrofuran, ethyl acetate, acetonitrile, dioxane and ethanol), water or a mixed solvent thereof, in the presence of a trapping reagent (such as tributyltin hydride, triethylsilane, dimedone, morpholine, diethylamine and pyrrolidine), an organic acid (such as acetic acid, formic acid and 2-ethylhexanoic acid) and/or a salt of an organic acid (such as sodium 2-ethylhexanoate and potassium 2-ethylhexanoate), in the presence or absence of a phosphine-based reagent (such as triphenylphosphine), by using a metal complex (such as tetrakis(triphenylphosphine)palladium (0), bis(triphenylphosphine)palladium (II) dichloride, palladium (II) acetate and chlorotris(triphenylphosphine)rhodium (I)), at 0 to 40° C.

In addition to the above-described methods, a deprotection reaction can be performed, for example, by a method described in T. W. Greene, Protective Groups in Organic Synthesis, Wiley, N.Y., 1999.

Examples of the protecting group of a hydroxy group include a methyl group, a trityl group, a methoxymethyl (MOM) group, a 1-ethoxyethyl (EE) group, a methoxyethoxymethyl (MEM) group, a 2-tetrahydropyranyl (THP) group, a trimethylsilyl (TMS) group, a triethylsilyl (TES) group, a t-butyldimethylsilyl (TBDMS) group, a t-butyldiphenylsilyl (TBDPS) group, an acetyl (Ac) group, a pivaloyl group, a benzoyl group, a benzyl (Bn) group, a p-methoxybenzyl group, an allyloxycarbonyl (Alloc) group, a 2,2,2-trichloroethoxycarbonyl (Troc) group and the like.

Examples of the protecting group of an amino group include a benzyloxycarbonyl group, a t-butoxycarbonyl group, an allyloxycarbonyl (Alloc) group, a 1-methyl-1-(4-biphenyl)ethoxycarbonyl (Bpoc) group, a trifluoroacetyl group, a 9-fluorenylmethoxycarbonyl group, a benzyl (Bn) group, a p-methoxybenzyl group, a benzyloxymethyl (BOM) group, a 2-(trimethylsilyl)ethoxymethyl (SEM) group and the like.

The protecting groups of a hydroxy group and an amino group are not particularly limited to those described above as long as the protecting groups can be eliminated easily and selectively. For example, the protecting groups described in T. W. Greene, Protective Groups in Organic Synthesis, Wiley, N.Y., 1999 are used.

In the present specification, the compound used as the starting material in each of the reactions, for example, the compound represented by general formula (A), (II), (III) or (IV) is known or can be easily prepared by a known method.

In the present specification, a reaction which involves heating in each of the reactions can be performed by using a water bath, an oil bath, a sand bath or a microwave as apparent to those skilled in the art.

In the present specification, a solid phase-supported reagent which is supported by a macromolecular polymer (such as polystyrene, polyacrylamide, polypropylene and polyethylene glycol) may be used appropriately, in each of the reactions.

In the present specification, the reaction product in each of the reactions can be purified by a conventional purification means. Examples of the purification means include distillation under a normal pressure or reduced pressure, high performance liquid chromatography which uses silica gel or magnesium silicate, thin-layer chromatography, an ion exchange resin, a scavenger resin, column chromatography, washing, recrystallization and the like. The purification may be performed at each of reactions or may be performed after the completion of several reactions.

[Toxicity]

The toxicity of the compound of the present invention is sufficiently low, and the compound of the present invention can be used as a pharmaceutical safely.

[Application to Pharmaceuticals]

The compound of the present invention has an $S1P_5$ (EDG-8) receptor agonist activity, and therefore, is useful as an agent for preventing and/or treating $S1P_5$-mediated disease. Examples of the $S1P_5$-mediated disease include neurodegenerative disease, autoimmune disease, infection, cancer and the like.

In addition, the compound of the present invention has an $S1P_5$ (EDG-8) receptor agonist activity, and therefore, is useful as an agent for preventing and/or treating cancer through the activating action of the tumor immunity.

In the present invention, examples of the neurodegenerative disease include anxiety-related disease (social anxiety disorder, anxiety neurosis, obsessive-compulsive disorder and Post-Traumatic Stress Disorder (PTSD)), polyglutamine disease, retinitis pigmentosa, neurosis, convulsion, panic disorder, sleep disorder, depression, reactive depression, epilepsy, Parkinson's disease, parkinsonian syndrome, Down's syndrome, schizophrenia, autonomic ataxia, Huntington's disease, Alzheimer's disease, affective disorder (including depressive disorder and bipolar disorder), cognitive impairment, migraine, tension-type headache, cluster headache, dissociative disorder, amyotrophic lateral sclerosis, neuromyelitis optica, optic neuritis, acute disseminated encephalomyelitis, allergic encephalomyelitis, Marchiafava-Bignami disease, Binswanger's disease, progressive multifocal leukoencephalopathy, postinfectious encephalitis, central pontine myelinolysis, adrenoleukodystrophy, multiple system atrophy, Krabbe disease, metachromatic leukodystrophy, Alexander's disease, Canavan disease, Cockayne syndrome, Pelizaeus-Merzbacher disease, Hurler's syndrome, Lowe syndrome, spinal cord injury, transverse myelitis, spinocerebellar degeneration, chronic inflammatory demyelinating polyradiculoneuropathy (CIDP), Guillain-Barre syndrome, phenylketonuria, Refsum's disease, Charcot-Marie-Tooth disease, Gaucher's disease, Niemann-Pick disease, multiple sclerosis, fragile X syndrome, autism, insomnia, nervous cough, psychogenic convulsive seizure, psychogenic syncopal attack, writer's cramp, spasmodic torticollis, neuropathy and the like.

In the present invention, examples of the autoimmune disease include inflammatory bowel disease, arthritis, lupus, rheumatism, psoriatic arthritis, osteoarthritis, Still's disease, juvenile arthritis, type 1 diabetes mellitus, myasthenia gravis, Hashimoto's thyroiditis, iodine thyroiditis, Basedow's disease, Sjogren's syndrome, Addison disease, opsoclonus-myoclonus syndrome, ankylosing spondylitis, antiphospholipid syndrome, aplastic anemia, autoimmune hepatitis, celiac disease, Goodpasture's syndrome, idiopathic thrombocytopenic purpura, scleroderma, primary biliary cirrhosis, Reiter's disease, Takayasu's arteritis, temporal arteritis, warm autoimmune hemolytic anemia, Wegener's granulomatosis, psoriasis, alopecia universalis, Behcet's disease, chronic fatigue syndrome, autonomic neuropathy, endometriosis, interstitial cystitis, myotonia, vulvodynia and systemic lupus erythematosus.

In the present invention, examples of the infection include symptoms which are developed by the infection of a normal cell in vivo with a pathogenic microorganism and proliferation of the pathogenic microorganism. Representative examples of the pathogenic microorganism include one or more kinds of a virus, a bacterium, a fungus and the like. The above-described pathogenic microorganism also includes a rickettsia, a chlamydia, a protozoan, a parasite and the like.

In the present invention, examples of the virus which causes infection include human hepatitis virus (such as hepatitis B virus, hepatitis C virus, hepatitis A virus and hepatitis E virus), human retrovirus, human immunodeficiency virus (such as HIV1 and HIV2), human T-cell leukemia virus or human T-lymphotropic virus (such as HTLV1 and HTLV2), herpes simplex virus type 1 or type 2, Epstein-Barr (EB) virus, cytomegalovirus, varicella-zoster virus, human herpesvirus (such as human herpesvirus 6), poliovirus, measles virus, rubella virus, Japanese encephalitis virus, mumps virus, influenza virus, common cold virus (such as adenovirus, enterovirus and rhinovirus), virus which causes severe acute respiratory syndrome (SARS), Ebola virus, West Nile virus, flavivirus, echovirus, Coxsackie virus, coronavirus, respiratory syncytial virus, rotavirus, norovirus, sapovirus, measles virus, parvovirus, vaccinia virus, HTL virus, dengue virus, papilloma virus, molluscum contagiosum virus, rabies virus, JC virus, arbovirus, encephalitis virus, hantavirus and Ebola virus.

In the present invention, examples of the bacterium which causes infection include *Vibrio cholerae, Salmonella enterica, Escherichia coli, Legionella, Bacillus anthracis, Helicobacter pylori, Listeria monocytogenes, Mycobacterium tuberculosis, nontuberculous mycobacteria, Staphylococcus, Streptococcus, Streptococcus pneumoniae, Neisseria meningitidis, Klebsiella pneumoniae, Serratia, Corynebacterium diphtheriae, Brucella, Bartonella hense-*

*lae, Erysipelothrix rhusiopathiae, Actinomyces, Borrelia burgdorferi, Clostridium perfringens, Shigella dysenteriae, Yersinia pestis, Clostridium tetani, Enterobacter* and the like.

In the present invention, examples of the fungus which causes infection include *Candida, Aspergillus, Cryptococcus, Blastomyces, Coccidioides, Histoplasma, Paracoccidioides* and *Sporothrix*.

In the present invention, examples of the protozoan which causes infection include *Plasmodium* and *Toxoplasma gondii*.

In the present invention, examples of the parasite which causes infection include *Entamoeba histolytica, Ascaris lumbricoides, Babesia, Cryptosporidium, Giardia lamblia, Ancylostoma, Enterobius vermicularis, Schistosoma, Cestoda, Trichinella spiralis* and *Trichuris trichiura*.

In the present invention, examples of other microorganisms which cause infection include *Mycoplasma* and *Spirochaeta*.

In the present invention, examples of cancer include cancer associated with cerebral nerve (such as pediatric brain tumors (for example, neuroblastoma, medulloblastoma, astrocytoma (juvenile pilocytic astrocytoma), ependymoma, craniopharyngioma, germ cell tumors, optic nerve glioma, choroid plexus papilloma and pontine glioma), adult brain tumors (for example, adult astrocytoma, adult malignant astrocytoma, adult glioblastoma, adult ependymoma, adult malignant ependymoma, adult malignant oligodendroglioma, adult medulloblastoma, adult meningioma and adult malignant meningioma), glioma (for example, astrocytoma, oligodendroglioma, ependymoma and brain stem glioma), pituitary adenoma, acoustic schwannoma, retinoblastoma and uveal malignant melanoma), respiratory tract cancer (such as pharyngeal cancer (for example, nasopharyngeal cancer, oropharyngeal cancer and hypopharyngeal cancer), laryngeal cancer, nasal sinus cancer, lung cancer (for example, small cell cancer and non-small-cell cancer), thymoma and mesothelioma), gastrointestinal cancer (such as esophageal cancer, gastric cancer, duodenal cancer and large bowel cancer (for example, colon cancer, rectal cancer and anal cancer)), oral cancer (such as gingival cancer, tongue cancer and salivary gland cancer), urinary system cancer (such as penile cancer, renal pelvis•ureter cancer, renal cell cancer, testicular tumor, prostate cancer and bladder cancer), cancers that affect women (such as vulvar cancer, uterine cancer (for example, cervical cancer and endometrial cancer), uterine sarcoma, trophoblastic disease (for example, hydatidiform mole, choriocarcinoma, placental-site trophoblastic tumor and persistent trophoblastic disease), vaginal cancer, breast cancer, breast sarcoma, ovarian cancer and ovarian germ cell tumor), skin cancer (such as melanoma (malignant melanoma) (for example, malignant lentiginous melanoma, superficial spreading melanoma, nodular melanoma, acral lentiginous melanoma and erosive melanoma), mycosis fungoides, squamous cell carcinoma, basal cell carcinoma, premonitory signs of skin cancer•intraepidermal carcinoma (for example, actinic keratosis, Bowen's disease and Paget's disease), lymphomatoid papulosis, cutaneous CD30 positive anaplastic large cell lymphoma, Sezary syndrome and cutaneous B-cell lymphoma), bone and muscle cancer (such as osteosarcoma, soft tissue sarcoma, rhabdomyosarcoma, synovial sarcoma and liposarcoma), thyroid cancer, carcinoid, liver cancer (hepatoma), hepatoblastoma, bile duct cancer, gallbladder cancer, pancreatic cancer, pancreatic endocrine tumors (such as insulinoma, gastrinoma and VIPoma), carcinoma of unknown primary, hereditary tumors•familial tumors (such as hereditary nonpolyposis colorectal cancer, familial adenomatous polyposis, hereditary breast and ovarian cancer syndrome, Li-Fraumeni syndrome, hereditary melanoma, Wilms' tumor, hereditary papillary renal cell carcinoma, von Hippel-Lindau syndrome and multiple endocrine neoplasia), leukemia (such as acute myeloid leukemia, acute lymphoblastic leukemia, myelodysplastic syndrome, chronic myeloid leukemia•chronic myeloproliferative disorder, adult T-cell leukemia-lymphoma, chronic lymphocytic leukemia and small lymphocytic lymphoma), multiple myeloma, primary macroglobulinemia, malignant lymphoma (such as Hodgkin's lymphoma, intermediate- and high-grade lymphomas, Burkitt's lymphoma, lymphoblastic lymphoma, follicular lymphoma, mantle-cell lymphoma, MALT (Mucosa-Associated Lymphoid Tissue) lymphoma and NK (natural killer) cell lymphoma) and the like.

The compound of the present invention may be administered as a combined medicine by being combined with other drug(s) for the purpose of:

1) complementation and/or enhancement of the preventing and/or treating effect of the compound,
2) improvement in kinetics•absorption, and reduction of the dose of the compound, and/or
3) reduction of the side effect of the compound.

The combined medicine of the compound of the present invention with other drug(s) may be administered in the form of a compounding agent in which both ingredients are compounded in a preparation or may be administered by means of separate preparations. The case of being administered by means of separate preparations includes concomitant administration and administrations with a time difference. In addition, in the case of the administrations with a time difference, the compound of the present invention may be firstly administered, followed by administration of the other drug(s). Alternatively, the other drug(s) may be firstly administered, followed by administration of the compound of the present invention. A method for administering the compound of the present invention and that for administering the other drug(s) may be the same or different.

The disease against which the above-described combined medicine exhibits the preventing and/or treating effect is not particularly limited as long as the disease is that against which the preventing and/or treating effect of the compound of the present invention is complemented and/or enhanced.

In addition, the combined medicine which is combined with the compound of the present invention includes not only those which have been found up to now but also those which will be found in future.

Examples of the other drug(s) for complementation and/or enhancement of the preventing and/or treating effect of the compound of the present invention on neurodegenerative disease include an acetylcholinesterase inhibitor, a nicotinic receptor modulator, a suppressor of production, secretion, accumulation, agglutination and/or deposition of β amyloid protein (such as a β secretase inhibitor, a γ secretase inhibitor, a drug having β amyloid protein agglutination inhibitory action, a β amyloid vaccine and a catabolic enzyme of β amyloid), an activator of brain function (such as an activator of brain metabolism and a cerebral circulation improving drug), a dopamine receptor agonist (a dopamine receptor stimulant), a dopamine release accelerating drug (a dopamine secretion accelerating drug or a dopamine release accelerating drug), a dopamine uptake inhibitor, a dopamine agonist, a dopamine antagonist, lithium carbonate, a serotonergic agonist, a serotonin antagonist (such as a 5-HT$_{2A}$ antagonist, a 5-HT$_3$ antagonist, a 5-HT$_4$ antagonist and a 5-HT$_7$ antagonist), a monoamine oxidase (MAO) inhibitor, an aromatic L-amino acid decarboxylase inhibitor (DCI), a norepinephrine (noradrenaline) supplement, an anticholinergic drug, a catechol-O-methyltransferase (COMT) inhibitor, a therapeutic drug for amyotrophic lateral sclerosis, a therapeutic drug for hyperlipidemia, an apoptosis inhibitor, a nerve regeneration•differentiation accelerating drug, an antihypertensive drug, a therapeutic drug for diabetes, a therapeutic drug for diabetic complication, an antidepressant (such as a tricyclic antidepressant and a tetracyclic antidepressant), an antianxiety drug, an antiepileptic drug, an anticonvulsant drug, an antispasmodic drug, a nonsteroidal antiinflammatory drug, an anti-cytokine drug (such as a TNF inhibitor and an MAP kinase inhibitor), a steroid, a sex hormone or a derivative thereof (such as progesterone, estradiol and estradiol benzoate), a thyroid hormone, a parathyroid hormone (such as PTH), a calcium channel blocker (a calcium antagonist), a calcium receptor antagonist, an opioid receptor agonist, an N-methyl-D-2-amino-5-D-aspartate (NMDA) receptor antagonist, a VR-1 receptor agonist, a neuromuscular junction blocking drug, a cannabinoid-2 receptor agonist, a GABAA receptor modulator (such as a GABAA receptor agonist), a GABAB receptor modulator, prostaglandins, a cholecystokinin antagonist, a nitric oxide synthase (NOS) inhibitor, a local anesthetic, a neurotrophic factor (such as neurotrophin, TGF-β superfamily, a neurokinin family and a growth factor), a sympathomimetic drug, a parasympathomimetic drug, a sympatholytic drug, a prostaglandin receptor antagonist, a prostaglandin receptor agonist, a carbonic anhydrase inhibitor, a hyperosmotic drug, a vasodilator drug, a metabolic activator, a diuretic drug (such as a thiazide diuretic drug, a loop diuretic drug and a potassium-sparing diuretic drug), a peripheral blood flow improving drug, an immunosuppressive drug, an immunoglobulin, an α-amino-3-hydroxy-5-methyl-4-isoxazolepropionic acid (AMPA)/kainic acid receptor antagonist, an Rho-kinase inhibitor, vitamins (such as vitamin B6 and vitamin B12), a cyclooxygenase (COX)-2 inhibitor, an antidizziness drug, a therapeutic drug for anemia, a therapeutic drug for heavy metal poisoning, a muscarinic receptor agonist, an aldose reductase inhibitor, a nerve regeneration accelerating drug, a protein kinase C (PKC) inhibitor, an advanced glycation end product (AGE) inhibitor, a reactive oxygen species scavenger, a muscle relaxant and the like.

Examples of the other drug(s) for complementation and/or enhancement of the preventing and/or treating effect of the compound of the present invention on autoimmune disease include an immunosuppressive drug, a steroid, a disease-modifying antirheumatic drug, an elastase inhibitor, a cannabinoid-2 receptor agonist, a prostaglandin, a prostaglandin synthase inhibitor, a phosphodiesterase inhibitor, a metalloprotease inhibitor, an adhesion molecule inhibitor, an anti-cytokine protein preparation such as an anti-TNF-α preparation, an anti-IL-1 preparation and an anti-IL-6 preparation, a cytokine inhibitor, a nonsteroidal antiinflammatory drug and an anti-CD 20 antibody.

Examples of the other drug(s) for complementation and/or enhancement of the preventing and/or treating effect of the compound of the present invention on infection include an antiviral drug, an antibiotic, an antifungal drug, an antiparasitic drug, an antiprotozoal drug and the like.

Examples of the other drug(s) for complementation and/or enhancement of the preventing and/or treating effect of the compound of the present invention on cancer include an alkylating drug, an antimetabolite, an anticarcinogenic antibiotic, a plant alkaloid drug, a hormonal drug, a platinum compound, an anti-CD 20 antibody and other anticancer agents.

The compound of the present invention is normally administered systemically or locally, in the form of an oral preparation or a parenteral preparation. Examples of the oral preparation include an oral liquid preparation (such as an elixir, a syrup, a pharmaceutically acceptable liquid agent, a suspension and an emulsion), an oral solid preparation (such as a tablet (including a sublingual tablet and an orally disintegrating tablet), a pill, a capsule (including a hard capsule, a soft capsule, a gelatin capsule and a microcapsule), a powdered agent, a granule and a lozenge) and the like. Examples of the parenteral preparation include a liquid preparation (such as an injection preparation (such as a subcutaneous injection preparation, an intravenous injection preparation, an intramuscular injection preparation, an intraperitoneal injection preparation and a preparation for drip infusion), an eye drop (such as an aqueous eye drop (such as an aqueous ophthalmic solution, an aqueous ophthalmic suspension, a viscous eye drop and a solubilized eye drop) and a non-aqueous eye drop (such as a non-aqueous ophthalmic solution and a non-aqueous ophthalmic suspension))), an external preparation (such as an ointment (such as an ophthalmic ointment)), an ear drop and the like. The above-described preparation may be a controlled-release preparation such as an immediate-release preparation and a sustained release preparation. The above-described preparation can be prepared by a known method, for example, by a method described in Pharmacopeia of Japan or the like.

The oral liquid preparation as an oral preparation is prepared, for example, by dissolving, suspending or emulsifying an active ingredient in a generally used diluent (such as purified water, ethanol and a mixed liquid thereof). In addition, the liquid preparation may further contain a wetting agent, a suspending agent, an emulsifying agent, a sweetening agent, a flavoring agent, a perfume, a preservative, a buffer agent and the like.

The oral solid preparation as an oral preparation is prepared, for example, by mixing an active ingredient with an excipient (such as lactose, mannitol, glucose, microcrystalline cellulose and starch), a bonding agent (such as hydroxypropyl cellulose, polyvinylpyrrolidone and magnesium aluminometasilicate), a disintegrating agent (such as calcium cellulose glycolate), a lubricant (such as magnesium stearate), a stabilizer, a solubilizing agent (such as glutamic acid and aspartic acid) and the like by a routine procedure. In addition, if necessary, the active ingredient may be coated with a coating agent (such as white soft sugar, gelatin, hydroxypropyl cellulose and hydroxypropyl methylcellulose phthalate) or may be coated with two or more layers.

The external preparation as a parenteral preparation is prepared by a known method or according to a normally used formulation. For example, an ointment is prepared by triturating or melting an active ingredient in a base. An ointment base is selected from those which are known and those which are normally used. For example, one selected from the followings is used or two or more kinds selected from the followings are used by being mixed together: a higher fatty acid or a higher fatty acid ester (such as adipic acid, myristic acid, palmitic acid, stearic acid, oleic acid, an adipate ester, a myristate ester, a palmitate ester, a stearate ester and an oleate ester), waxes (such as beeswax, whale wax and ceresin), a surface-active agent (such as a polyoxyethylene alkyl ether phosphoric ester), a higher alcohol (such as cetanol, stearyl alcohol and cetostearyl alcohol), a silicone oil (such as dimethyl polysiloxane), hydrocarbons (such as hydrophilic petrolatum, white petrolatum, purified lanolin and liquid paraffin), glycols (such as ethylene glycol, diethylene glycol, propylene glycol, polyethylene glycol and macrogol), a vegetable oil (such as castor oil, olive oil, sesame oil and turpentine oil), an animal oil (such as mink oil, egg-yolk oil, squalane and squalene), water, an absorption promoter and an agent for preventing skin rash. In addition, a moisturizing agent, a preservative, a stabilizing agent, an antioxidant, a flavoring agent and the like may be contained.

The injection preparation as a parenteral preparation includes a solution, a suspension, an emulsion and a solid injection preparation which is used at the time of use by being dissolved or suspended in a solvent. The injection preparation is used, for example, by dissolving, suspending or emulsifying an active ingredient in a solvent. Examples of the solvent used include distilled water for injection, saline, a vegetable oil, alcohols such as propylene glycol, polyethylene glycol and ethanol and the like as well as a mixture thereof. In addition, the injection preparation may contain a stabilizer, a solubilizing agent (such as glutamic acid, aspartic acid and polysorbate 80 (registered trademark)), a suspending agent, an emulsifying agent, an analgesic, a buffer agent, a preservative and the like. The above-described injection preparation is prepared by being sterilized at the final process or by an aseptic manipulation method. In addition, the above-described injection preparation can be also used by preparing a sterile solid preparation, for example, a lyophilized preparation, and dissolving the sterile solid preparation in sterilized or sterile distilled water for injection or other solvent before use of the preparation.

In order to use the compound of the present invention or the combined medicine of the compound of the present invention with other drug(s) for the above-described purpose, the compound of the present invention or the combined medicine of the compound of the present invention with other drug(s) is normally administered systemically or locally, in the form of an oral preparation or a parenteral preparation. The dose varies depending on the age, the body weight, the symptom, the therapeutic effect, the method for administration, the duration of the treatment and the like. However, normally, the dose per adult is in the range of from 1 ng to 1,000 mg per administration, from one to several oral administrations per day or the dose per adult is in the rage of from 0.1 ng to 10 mg per administration, from one to several parenteral administrations per day. Alternatively, the dose is continuously administrated intravenously for a period of time in the range of 1 to 24 hours per day. Of course, the dose varies depending on various factors as described above, and therefore, there are some cases in which a dose below the above-described dose is sufficient and there are other cases in which administration of a dose which exceeds the above-described range is required.

EXAMPLES

The present invention will be described in details by referring to Examples hereinbelow, but the present invention is not limited to Examples.

Concerning chromatographic separation or TLC, a solvent in parentheses corresponds to an eluting solvent or a developing solvent employed and a ratio is expressed by volume ratio.

Concerning NMR, a solvent in parentheses corresponds to a solvent used for the measurement.

A compound name used in the present specification is given by using a computer program ACD/Name (registered trademark) of Advanced Chemistry Development which generally denominates a compound according to the IUPAC nomenclature or by denomination according to the IUPAC nomenclature.

LC-MS/ELSD was performed by any of the following conditions:

Condition A: {column: Waters ACQUITY $C_{18}$ (particle size: $1.7 \times 10^{-6}$ m; column length: 30×2.1 mm I.D.); flow rate: 1.0 mL/min; column temperature: 40° C.; mobile phase (A): 0.1% formic acid aqueous solution; mobile phase (B): 0.1% formic acid-acetonitrile solution; gradient (the ratio of mobile phase (A):mobile phase (B) is described): [0 min] 95:5; [0.1 min] 95:5; [1.2 min] 5:95; [1.4 min] 5:95; [1.41 min] 95:5; [1.5 min] 95:5; Detector: UV(PDA), ELSD, MS} or Condition B {column: Luna C18 (column length: 250×4.6 mm I.D.); flow rate: 1.0 mL/min; mobile phase (A): 0.1% trifluoroacetic acid aqueous solution; mobile phase (B): 0.1% trifluoroacetic acid-acetonitrile solution; gradient (the ratio of mobile phase (A):mobile phase (B) is described): [0 min] 90:10; [0.1 min] 0:100; [20 min] 0:100; [25 min]; detector: UV(PDA), ELSD, MS}.

Example 1

6-(Benzyloxy)-3,4-dihydronaphthalen-1(2H)-one

To a solution of 6-hydroxy-3,4-dihydronaphthalen-1(2H)-one (CAS registry number: 3470-50-6) (24.3 g) in acetone (160 mL), benzyl bromide (29.4 mL) and potassium carbonate (31.1 g) were added at room temperature and the mixture was stirred at 40° C. for 3.5 hours. After insoluble matters were filtered off, the mixture was concentrated and washed with a mixed solvent of tert-butyl methyl ether (MTBE)-hexane (1:4) to give the title compound (34.5 g) having the following physical property.

TLC: Rf 0.38 (hexane:ethyl acetate=3:1).

Example 2

7-(Benzyloxy)-4-methyl-1,2-dihydronaphthalene

To a solution of the compound (34.5 g) prepared in Example 1 in tetrahydrofuran (THF) (300 mL), methylmagnesium bromide (3 mol/L solution in diethyl ether, 55 mL) was added at 0° C., and the mixture was stirred at room temperature for 1 hour. The reaction liquid was cooled to 0° C. and was poured to ice-saturated ammonium chloride aqueous solution, and 2 mol/L hydrochloric acid was added to the mixture, and the mixture was stirred at room temperature for 3 hours. The mixture was extracted with ethyl acetate, and the organic layer was washed sequentially with water and saturated saline, was dried and then was concentrated. The obtained residue was purified by silica gel column chromatography (hexane:ethyl acetate=10:1) to give the title compound (24.8 g) having the following physical property.

TLC: Rf 0.57 (hexane:ethyl acetate=15:1).

Example 3

6-(Benzyloxy)-1-methyl-3,4-dihydronaphthalene-2-carbaldehyde

To phosphorus oxychloride (26.7 g), N,N-dimethylformamide (DMF) (60 mL) was added dropwise at 0° C., and the mixture was stirred for 20 minutes. To the mixture, a solution of the compound (24.8 g) prepared in Example 2 in methylene chloride (60 mL) was added dropwise slowly, and the mixture was stirred at room temperature for 90 minutes. The reaction liquid was cooled to 0° C., was poured to ice and was left for some time, and then was extracted with a mixed solvent of hexane-ethyl acetate (1:2). The organic layer was washed sequentially with water and saturated saline, was dried and then was concentrated. The obtained solid was washed with MTBE to give the title compound (19.9 g) having the following physical property.

TLC: Rf 0.50 (hexane:ethyl acetate=3:1).

Example 4

6-Hydroxy-1-methyl-3,4-dihydronaphthalene-2-carbaldehyde

To thioanisole (35 mL), trifluoroacetic acid (140 mL) was added at 0° C., and to the mixture, the compound (9.17 g) prepared in Example 3 was added little by little, and the mixture was stirred at room temperature for 4 hours. The reaction liquid was poured to ice, and 5 mol/L sodium hydroxide aqueous solution was added to the reaction solution and the mixture was washed with MTBE. To the aqueous layer, 1 mol/L hydrochloric acid was added, and the mixture was extracted with ethyl acetate. The organic layer was dried, and then was concentrated. The obtained residue was purified by silica gel column chromatography (hexane: ethyl acetate=5:1 to 2:1) to give the title compound (6.03 g) having the following physical property.

TLC: Rf 0.26 (hexane:ethyl acetate=3:1).

Example 5

Methyl 1-[(6-hydroxy-1-methyl-3,4-dihydronaphthalen-2-yl)methyl]azetidine-3-carboxylate Under a nitrogen atmosphere, a mixture of the compound (2.60 g) prepared in Example 4, methyl azetidine-3-carboxylate hydrochloride (3.14 g) and triethylamine (6.29 g) in THF was treated with sodium triacetoxyborohydride (2.92 g) at 0° C., and the obtained mixture was returned to room temperature for over 17 hours. Thereafter, to the reaction solution, ethyl acetate (300 mL) was poured and the mixture was washed sequentially with saturated sodium bicarbonate aqueous solution, water and saturated saline. The organic layer was dried over sodium sulfate and was concentrated under a reduced pressure. The obtained residue was purified by silica gel column chromatography (50-80% ethyl acetate/hexane) to give the title compound (3.21 g) having the following physical properties.

$^1$H-NMR (CDCl$_3$): δ7.10, 6.63, 6.57, 3.70, 3.58, 3.37-3.31, 2.60, 2.25-2.22, 2.07; MS (M+H): 288.

Example 6

Methyl 1-{[6-(cyclopentyloxy)-1-methyl-3,4-dihydro-2-naphthalenyl]methyl}-3-azetidinecarboxylate

[Chemical Formula 15]

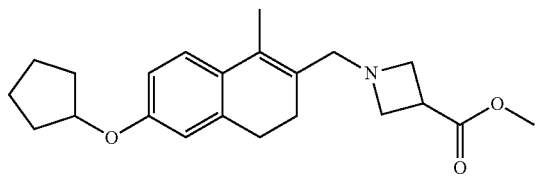

A solution (3 mL) of the compound (97 mg) prepared in Example 5 in DMF was treated with sodium hydride (60% mineral oil mixture) (14 mg), and the mixture was stirred under a nitrogen atmosphere at room temperature for 15 minutes. The obtained solution was treated with bromocyclopentane (49 mg), and the mixture was stirred for 18 hours. Thereafter, the reaction mixture was diluted with ethyl acetate, was washed with water and 5% lithium chloride aqueous solution, was dried over sodium sulfate, and thereafter, was concentrated under a reduced pressure. The residue was purified by silica gel column chromatography (20-80% ethyl acetate/hexane) to give the title compound (51 mg) having the following physical properties.

$^1$H-NMR (CDCl$_3$): δ7.17, 6.69, 6.65, 4.76-4.73, 3.70, 3.55-3.52, 3.35-3.27, 2.67, 2.26, 2.08, 1.92-1.77, 1.64-1.59; MS (M+H): 356.

Example 7

1-{[6-(Cyclopentyloxy)-1-methyl-3,4-dihydro-2-naphthalenyl]methyl}-3-azetidinecarboxylic acid

[Chemical Formula 16]

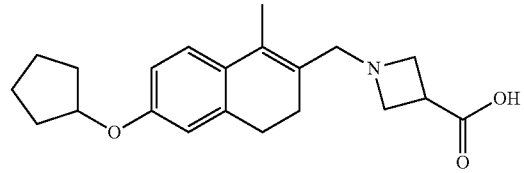

A solution (3 mL) of the compound (45 mg) prepared in Example 6 in methanol was treated with 2N sodium hydroxide (0.44 mL) and the mixture was stirred at room temperature for 45 minutes. Thereafter, the reaction solution was concentrated under a reduced pressure and was purified by silica gel column chromatography (methylene chloride: methanol:concentrated aqueous ammonia=80:18:2) to give the title compound (35 mg) having the following physical properties.

$^1$H-NMR (DMSO-d$_6$): δ7.14, 6.70, 6.67, 4.80-4.77, 3.40, 3.20-3.18, 2.58, 2.16, 2.01, 1.92-1.86, 1.71-1.65, 1.60-1.55; MS (M+H): 342.

Examples 7 (1) to 7 (3)

A procedure for a purpose similar to that for Example 6 to Example 7 was carried out by using the compound prepared in Example 5 and a corresponding brominated compound instead of bromocyclopentane to give the following compounds of Examples.

Example 7 (1)

1-{[6-(Cycloheptyloxy)-1-methyl-3,4-dihydro-2-naphthalenyl]methyl}-3-azetidinecarboxylic acid $^1$H-NMR (DMSO-d$_6$): δ7.14, 6.69, 6.66, 4.49-4.45, 3.38, 3.18-3.17, 2.58, 2.15, 2.01, 1.96-1.90, 1.70-1.62, 1.57-1.52, 1.47-1.43;

MS (M+H): 370.

Example 7 (2)

1-({1-Methyl-6-[(cis-4-methylcyclohexyl)oxy]-3,4-dihydro-2-naphthalenyl}methyl)-3-azetidinecarboxylic acid $^1$H-NMR (CD$_3$ COOD): δ7.29, 6.78, 6.75, 4.63-4.18, 3.80, 2.71, 2.29, 2.21, 2.03-1.96, 1.63-1.36, 0.94;
MS (M+H): 370.

Example 7 (3)

1-{[6-(3-Cyclopenten-1-yloxy)-1-methyl-3,4-dihydro-2-naphthalenyl]methyl}-3-azetidinecarboxylic acid (LC-MS/ELSD): (Retention time: 0.77 minute, Condition A);
MS (M+H): 340.

Example 8: Methyl

1-{[6-(4-fluorophenoxy)-1-methyl-3,4-dihydronaphthalen-2-yl]methyl}azetidine-3-carboxylate Under a nitrogen atmosphere, a mixed solution (5 mL) of the compound (300 mg) prepared in Example 4, cyclohexanol (335 mg) and triphenylphosphine in THF was treated with diisopropyl azodicarboxylate (DIAD) (643 mg) and the obtained mixture was stirred at room temperature for 30 minutes. Thereafter, the reaction solution was concentrated under a reduced pressure and the obtained residue was purified by silica gel column chromatography (0-10% ethyl acetate/hexane) to give the title compound (253 mg) having the following physical properties.

$^1$H-NMR (CDCl$_3$): δ10.32, 7.46, 6.79, 6.74, 4.33-4.29, 2.71, 2.52-2.50, 2.00-1.98, 1.83-1.80, 1.60-1.51, 1.43-1.38.

Example 9

(3R)-1-{[6-(Cyclohexyloxy)-1-methyl-3,4-dihydro-2-naphthalenyl]methyl}-3-pyrrolidinecarboxylic acid

[Chemical Formula 17]

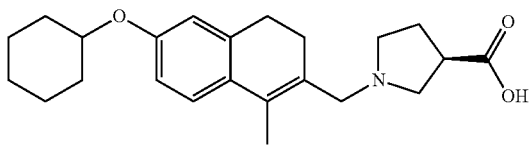

A mixed solution (2 mL) of the compound (60 mg) prepared in Example 8 and (R)-pyrrolidine-3-carboxylic acid (51 mg) in methanol was treated with sodium cyanoborohydride (28 mg), and the obtained mixture was stirred at 60° C. for 30 minutes. Thereafter, the reaction solution was concentrated under a reduced pressure, and the obtained residue was purified by silica gel column chromatography (methylene chloride:methanol:concentrated aqueous ammonia=80:18:2), and thereafter, lyophilization was performed with acetonitrile/water to give the title compound (63 mg) having the following physical properties.

$^1$H-NMR (CD$_3$ COOD): δ7.28, 6.77-6.74, 4.36-4.27, 4.15, 3.94-3.30, 2.73, 2.52-2.36, 2.17, 2.00-1.95, 1.80-1.78, 1.57-1.27;
(LC-MS/ELSD): (Retention time: 15.10 minutes).

Examples 9 (1) to 9 (3)

A procedure for a purpose similar to that for Example 8 to Example 9 was carried out by using the compound prepared in Example 4 or a corresponding aldehyde derivative instead of the compound prepared in Example 4, a corresponding carboxylic acid derivative instead of (R)-pyrrolidine-3-carboxylic acid and bromocyclopentane to give the following compounds of Examples.

Example 9 (1)

(3S)-1-{[6-(Cyclohexyloxy)-1-methyl-3,4-dihydro-2-naphthalenyl]methyl}-3-pyrrolidinecarboxylic acid $^1$H-NMR (CD$_3$COOD): δ7.28, 6.77, 6.74, 4.35-4.28, 4.15, 3.90-3.32, 2.73, 2.52-2.38, 2.17, 2.01-1.95, 1.80-1.78, 1.57-1.30;
(LC-MS/ELSD): (Retention time: 15.14 minutes, Condition B).

Example 9 (2)

1-{[6-(Cyclohexyloxy)-3,4-dihydro-2-naphthalenyl]methyl}-3-azetidinecarboxylic acid

[Chemical Formula 18]

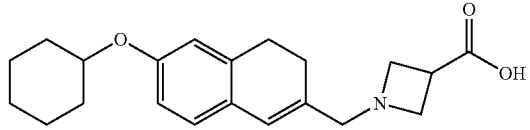

$^1$H-NMR (CD$_3$COOD): δ7.00, 6.72, 6.62, 4.61-4.19, 3.99, 3.82, 2.79, 2.31, 1.96, 1.78, 1.58-1.30;
(LC-MS/ELSD): (Retention time: 14.33 minutes).

Example 9 (3)

1-{[6-(Cyclohexyloxy)-1-methyl-3,4-dihydro-2-naphthalenyl]methyl}-3-methyl-3-pyrrolidinecarboxylic acid (LC-MS/ELSD): (Retention time: 0.82 minutes, Condition A);
MS (M+H): 382.

Example 10

Methyl 1-{[6-(4-fluorophenoxy)-1-methyl-3,4-dihydronaphthalen-2-yl]methyl}azetidine-3-carboxylate A mixture of the compound (162 mg) prepared in Example 5 and cesium carbonate (184 mg) was treated with a solution of 0.04 M 2,2,6,6-tetramethylheptane-3,5-dione in N-methylpyrrolidinone (0.71 mL), and thereafter, the mixture was treated sequentially with 1-fluoro-4-iodobenzene (139 mg) and copper (I) chloride (14 mg). Under an argon atmosphere, the obtained mixture was sealed, and was stirred at 120° C. for 15.5 hours. Thereafter, the reaction product was cooled to room temperature, ethyl acetate was poured to the reaction product, and the reaction product was washed sequentially with concentrated aqueous ammonia, water and saturated saline. The organic layer was dried over sodium sulfate, the obtained solution was concentrated under a reduced pressure, and the obtained residue was purified by silica gel column chromatography (2-6% methanol/methylene chloride) to give the title compound (68 mg) having the following physical properties.
$^1$H-NMR (CDCl$_3$) δ: 7.22, 7.04-6.96, 6.78, 6.73, 3.71, 3.56-3.29, 2.66, 2.28, 2.10;
MS (M+H): 382.

Example 11

1-{[6-(4-Fluorophenoxy)-1-methyl-3,4-dihydro-2-naphthalenyl]methyl}-3-azetidinecarboxylic acid

[Chemical Formula 19]

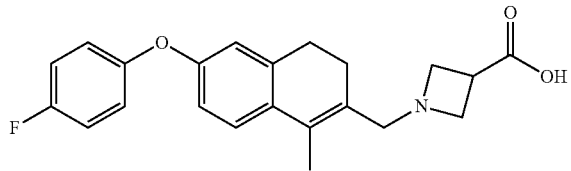

A solution (4 mL) of the compound (61 mg) prepared in Example 10 in methanol was treated with 3 M sodium hydroxide aqueous solution (0.373 mL), and the mixture was stirred at room temperature for 35 minutes. Thereafter, the reaction product was concentrated under a reduced pressure and the obtained residue was purified by silica gel column chromatography (methylene chloride:methanol:concentrated aqueous ammonia=80:18:2) to give the title compound (48 mg) having the following physical properties.
$^1$H-NMR (CD$_3$COOD): δ7.36, 7.12-7.02, 6.82-6.80, 4.64-4.20, 3.81, 2.72, 2.32, 2.23;
(LC-MS/ELSD): (Retention time: 14.18 minutes, Condition B).

Examples 11 (1) to 11 (3)

A procedure for a purpose similar to that for Example 10 to Example 11 was carried out by using the compound prepared in Example 5 and a corresponding benzene derivative instead of 1-fluoro-4-iodobenzene to give the following compounds of Examples.

Example 11 (1)

1-[(1-Methyl-6-phenoxy-3,4-dihydro-2-naphthalenyl)methyl]-3-azetidinecarboxylic acid $^1$H-NMR (CD$_3$COOD): δ7.73-7.33, 7.12, 7.04-7.02, 6.85-6.83, 4.65-4.21, 3.82, 2.72, 2.32, 2.23;
(LC-MS/ELSD): (Retention time: 14.09 minutes, Condition B).

Example 11 (2)

1-{[6-(3-Fluorophenoxy)-1-methyl-3,4-dihydro-2-naphthalenyl]methyl}-3-azetidinecarboxylic acid TLC: Rf 0.51 (n-butanol:ethanol:water=4:1:1);
$^1$H-NMR (CD$_3$ OD) δ7.46-7.30, 6.92-6.69, 4.28-4.11, 3.50-3.37, 2.75, 2.27, 2.24.

Example 11 (3)

1-({1-Methyl-6-[3-(trifluoromethyl)phenoxy]-3,4-dihydro-2-naphthalenyl}methyl)-3-azetidinecarboxylic acid TLC: Rf 0.52 (chloroform:methanol=3:1);
$^1$H-NMR (CD$_3$OD): δ7.52, 7.40, 7.20, 6.88, 4.10-3.82, 3.38, 2.78, 2.38-2.20.

Example 12

Methyl

1-[(methyl-6-{[(trifluoromethyl)sulfonyl]oxy}-3,4-dihydronaphthalen-2-yl)methyl]azetidine-3-carboxylate To a solution of the compound (5 g) prepared in Example 5 in dichloromethane (35 mL), 1,1,1-trifluoro-N-phenyl-N-(trifluoromethylsulfonyl)methanesulfonamide (6.84 g) and diisopropylethylamine (DIPEA) (3.45 mL) were added, and the mixture was stirred at room temperature. After 3 hours, the starting material remained, and therefore, 1,1,1-trifluoro-N-phenyl-N-(trifluoromethylsulfonyl)methanesulfonamide (3.10 g) and DIPEA (3.45 mL) were added to the mixture, and the mixture was stirred at room temperature for 1 hour. The mixture was extracted by adding dichloromethane and water, the organic layer was washed with saturated saline, and thereafter, was dried over sodium sulfate. After concentration under a reduced pressure, the residue was purified by aminosilica gel column chromatography (hexane:ethyl acetate=100:0 to 90:10) to give the title compound (6.8 g) having the following physical properties.
$^1$H-NMR (CDCl$_3$): δ 7.29, 7.08, 7.01, 3.71, 3.59-3.52, 3.41-3.27, 2.73, 2.31, 2.10.

Example 13

Methyl 1-{[1-methyl-6-(4,4,5,5-tetramethyl-1,3,2-dioxaborolan-2-yl)-3,4-dihydronaphthalen-2-yl]methyl}azetidine-3-carboxylate To a solution of the compound (2 g) prepared in Example 12 in dioxane (20 mL), bis(pinacolato)diboron (1.5 g), potassium acetate (1.4 g) and 1,1'-bis(diphenylphosphino)ferrocene palladium (II) dichloride dichloromethane complex (PdCl$_2$ (dppf)-CH$_2$ Cl$_2$) (390 mg) were added, and the mixture was heated under stirring at 80° C. overnight. To the mixture, water and ethyl acetate were added, and the mixture was filtered through Celite and the filtrate was extracted with ethyl acetate. The organic layer was washed with saturated saline and was dried over sodium sulfate. After concentration under a reduced pressure, the product was roughly purified by silica gel column chromatography (dichloromethane:methanol=100:0 to 90:10) to give the title compound (2.75 g) having the following physical properties.
$^1$H-NMR (CDCl$_3$): δ7.67, 7.58, 7.31, 4.11-4.03, 3.75, 3.74-3.55, 2.74, 2.29, 2.18, 1.35.

Example 14

1-({1-Methyl-6-[2-(trifluoromethyl)phenyl]-3,4-dihydro-2-naphthalenyl}methyl)-3-azetidinecarboxylic acid

[Chemical Formula 20]

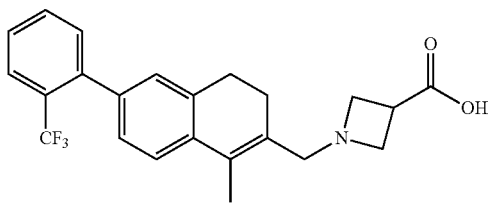

To a solution of the compound (160 mg) prepared in Example 13 in dioxane (1 mL), 2-bromobenzotrifluoride (75 mg), 2 M potassium phosphate (0.4 mL) and bis(tri-tert-butylphosphine)palladium (0) (Pd(tBu$_3$ P)$_2$) (23 mg) were added, and the mixture was heated under stirring at 90° C. overnight. To the mixture which was concentrated under a reduced pressure, THF (1.5 mL) and 2 N sodium hydroxide (0.7 mL) were added, and the mixture was stirred at room temperature for 2 hours. To the mixture, 2 N hydrochloric acid (1.1 mL) was added and the mixture was concentrated under a reduced pressure, and thereafter, was purified by PLC silica gel plate (chloroform:methanol:water=50:20:1) to give the title compound (52 mg) having the following physical properties.

TLC: Rf 0.49 (n-butanol:ethanol:water=4:1:1);
$^1$H-NMR (CD$_3$OD): δ7.76, 7.63, 7.52, 7.40, 7.35, 7.17, 7.09, 4.02-3.93, 3.90-3.78, 3.42-3.36, 2.77, 2.31, 2.24.

Examples 14 (1) to 14 (4)

A procedure for a purpose similar to that for Example 10 to Example 11 was carried out by using the compound prepared in Example 5 and a corresponding halogenated cyclic compound instead of 2-bromobenzotrifluoride to give the following compounds of Examples.

Example 14 (1)

1-[(1-Methyl-6-phenyl-3,4-dihydro-2-naphthalenyl)methyl]-3-azetidinecarboxylic acid TLC: Rf 0.23 (n-butanol:ethanol:water=4:1:0.2);
$^1$H-NMR (CD$_3$ OD): δ 7.62, 7.50-7.28, 7.16, 3.57, 3.50-3.18, 2.74, 2.38-2.10.

Example 14 (2)

1-({1-Methyl-6-[3-(trifluoromethyl)phenyl]-3,4-dihydro-2-naphthalenyl}methyl)-3-azetidinecarboxylic acid

[Chemical Formula 21]

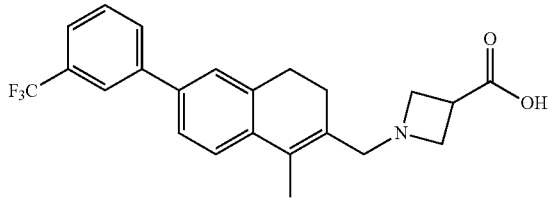

TLC: Rf 0.47 (n-butanol:ethanol:water=4:1:1);
$^1$H-NMR (CD$_3$ OD): δ 7.95-7.89, 7.67-7.63, 7.57-7.54, 7.49, 4.26-4.08, 3.42-3.35, 2.86, 2.32, 2.28.

Example 14 (3)

1-{[1-Methyl-6-(2-pyridinyl)-3,4-dihydro-2-naphthalenyl]methyl}-3-azetidinecarboxylic acid

[Chemical Formula 22]

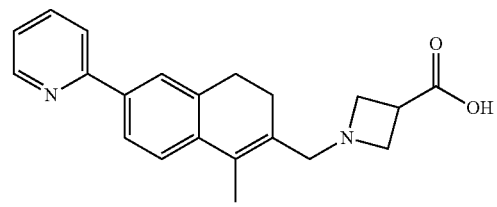

TLC: Rf 0.32 (n-butanol:ethanol:water=4:1:1);
$^1$H-NMR (CD$_3$OD) δ8.61-8.57, 7.90-7.86, 7.80, 7.74, 7.48, 7.38-7.32, 4.00-3.92, 3.88-3.79, 3.39-3.37, 2.84, 2.32, 2.24.

Example 14 (4)

1-[(5'-Methyl-7',8'-dihydro-1,2'-binaphthalen-6'-yl)methyl]-3-azetidinecarboxylic acid TLC: Rf 0.29 (chloroform:methanol=5:1);
$^1$H-NMR (CD$_3$OD)β7.94-7.84, 7.56-7.38, 7.31, 7.24, 3.93-3.84, 3.80-3.66, 3.37-3.32, 2.81, 2.34, 2.26.

Example 15

Ethyl 4-(3-methoxyphenyl)-3-methylbutanoate 1-(3-Methoxyphenyl)propan-2-one (CAS registry number: 3027-13-2) (15 g) was dissolved in THF (1,000 mL), and to the mixture, sodium hydride (4.4 g) was added little by little at 0° C. While being left at 0° C., after the mixture was stirred for 15 minutes, ethyl (2-diethoxyphosphoryl) acetate (24.57 g) was added, and the mixture was warmed to room temperature and stirred for 8 hours. After being diluted with ethyl acetate, the mixture was washed sequentially with tap water and saturated saline, was dried over anhydrous magnesium sulfate, and thereafter, the solvent was distilled off. The residue was diluted with ethyl acetate (1,000 mL), and to the residue, 5% palladium carbon (100 mg) was added, and the mixture was stirred under hydrogen atmosphere at room temperature for 4 hours. The reaction liquid was filtered through Celite and the solvent was distilled off. The product was purified by silica gel column chromatography (hexane:ethyl acetate=10:1) to give the title compound (5.7 g) having the following physical properties.

$^1$H-NMR (CDCl$_3$) δ7.19, 6.75, 4.11, 3.80, 2.60, 2.49, 2.38-2.20, 2.18, 1.26, 0.94.

Example 16

4-(3-Methoxyphenyl)-3-methylbutanoic acid

The compound (5.7 g) prepared in Example 15 was dissolved in THF (50 mL), and to the mixture, 2 N sodium hydroxide aqueous solution (24 mL) was added, and the mixture was stirred at room temperature for 2 hours. The mixture was neutralized with the same amount of hydrochloric acid, and thereafter, the solvent was distilled off, and the mixture was diluted with ethanol and was desalted by filtration to give the title compound (4.7 g) having the following physical properties.

$^1$H-NMR (CDCl$_3$): δ7.18, 6.72, 3.80, 2.62, 2.50, 2.50-2.10, 0.98.

Example 17

6-Methoxy-3-methyl-3,4-dihydronaphthalen-1(2H)-one

The compound (4.7 g) prepared in Example 16 was dissolved in dichloromethane (120 mL), and DMF (10 μL) was added to the mixture. Oxalyl chloride (2.9 g) was added dropwise to the mixture at 0° C. The reaction solution was warmed to room temperature, and was stirred for 2 hours, and thereafter, the solvent was distilled off to give 4-(3-methoxyphenyl)-3-methylbutanoyl chloride. The compound was dissolved in dichloromethane (120 mL) as it was, and to the mixture, ammonium chloride (3.74 g) was added at 0° C. The reaction solution was warmed to room temperature, and was stirred for 4 hours. The reaction solution was poured to ice water, and the organic layer was separated. The organic layer was dried over anhydrous sodium sulfate, and thereafter, the solvent was distilled off. The product was purified by silica gel column chromatography (hexane:ethyl acetate=10:1) to give the title compound (3.6 g) having the following physical properties.

$^1$H-NMR (CDCl$_3$): δ8.00, 6.82, 6.69, 3.86, 2.85, 2.75-2.60, 2.40-2.22, 1.12.

Example 18

1-(6-Methoxy-3-methyl-3,4-dihydronaphthalen-2-yl)ethanone

The compound (1 g) prepared in Example 17 was dissolved in methanol (100 mL), and sodium borohydride (398 mg) was added at 0° C. to the mixture. The reaction solution was warmed to room temperature and was stirred for 2 hours, and thereafter, ammonium chloride aqueous solution was added to the reaction solution, and the reaction solution was extracted with ethyl acetate, and the organic layer was washed with saturated saline and was dried over anhydrous sodium sulfate, and thereafter, the solvent was distilled off. The product was roughly purified by silica gel column chromatography (hexane:ethyl acetate=10:1), and was used for the next reaction as it was. The roughly purified product was dissolved in DMF (100 mL), and oxalyl chloride (2.2 g) was added to the mixture. The reaction solution was heated to 60° C. and was stirred for 8 hours. Thereafter, the reaction solution was added to ice water, and the mixture was stirred for 5 minutes, and thereafter, the organic layer was separated. The organic layer was washed with saturated saline, and thereafter, was dried over anhydrous sodium sulfate, and the solvent was distilled off. The product was purified by silica gel column chromatography (hexane:ethyl acetate=10:1 to 5:1) to give the title compound (299 mg) having the following physical properties.

$^1$H-NMR (CDCl$_3$): δ9.57, 7.30-7.24, 6.82-6.78, 3.85, 3.08, 2.65, 0.92.

Example 19

6-Hydroxy-3-methyl-3,4-dihydronaphthalene-2-carbaldehyde

The compound (299 mg) prepared in Example 18 was dissolved in dichloromethane (100 mL), and boron tribromide (815 mg) was added dropwise at 0° C. to the mixture. The mixture was stirred as it was for 3 hours, and thereafter, the reaction solution was added to ice water, and the mixture was stirred for 5 minutes, and thereafter, the organic layer was separated. The organic layer was washed with saturated saline, and thereafter, was dried over anhydrous sodium sulfate, and the solvent was distilled off. The product was purified by silica gel column chromatography (hexane:ethyl acetate=5:1) to give the title compound (200 mg) having the following physical properties.

$^1$H-NMR (CDCl$_3$): δ9.57, 7.18, 6.72, 3.08, 2.60, 0.94.

Example 20

Methyl 1-[(6-hydroxy-3-methyl-3,4-dihydronaphthalen-2-yl)methyl]azetidine-3-carboxylate The compound (200 mg) prepared in Example 19 was dissolved in DMF (40 mL), and to the mixture, triethylamine (0.15 mL) was added, and then methyl azetidine-3-carboxylate hydrochloride (161 mg) was added. To the mixture, sodium triacetoxyborohydride (225 mg) was added at room temperature, and the mixture was stirred as it was at room temperature for 8 hours. The mixture was diluted with ethyl acetate, and thereafter, was washed with water, and further, the organic layer was washed with saturated saline, and thereafter, was dried over anhydrous sodium sulfate, and the solvent was distilled off. The product was purified by aminosilica gel column chromatography (hexane:ethyl acetate=10:1 to 1:1) to give the title compound (121 mg) having the following physical properties.

$^1$H-NMR (CDCl$_3$): δ6.84, 6.58, 6.21, 3.80-3.22, 3.08, 2.80, 2.50-2.30, 0.90.

Example 21

1-{[6-(Cyclohexyloxy)-3-methyl-3,4-dihydro-2-naphthalenyl]methyl}-3-azetidinecarboxylic acid

[Chemical Formula 23]

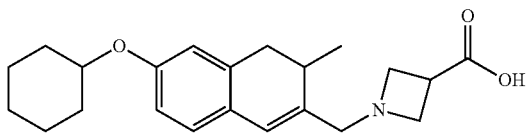

A procedure for a purpose similar to that for Example 6 was carried out by using the compound (30 mg) prepared in Example 20 and cyclohexanol (10 mg) to give the title compound (7.7 mg) having the following physical properties.

TLC: Rf 0.22 (chloroform:methanol=3:1);

$^1$H-NMR (CD$_3$ OD): δ6.96, 6.68, 6.36, 4.28, 4.0-3.80, 3.80-3.60, 3.45-3.10, 2.98, 2.58, 2.38, 1.96, 1.78, 1.62-1.28, 0.92.

Examples 21 (1) to 21 (2)

A procedure for a purpose similar to that for Example 18→Example 19→Example 20→Example 21 was carried out by using a corresponding cyclic ketone compound instead of the compound prepared in Example 17, methyl azetidine-3-carboxylate hydrochloride and cyclohexanol to give the following compounds of Examples.

Example 21 (1)

1-{[6-(Cyclohexyloxy)-1,3-dimethyl-3,4-dihydro-2-naphthalenyl]methyl}-3-azetidinecarboxylic acid $^1$H-NMR (CD$_3$ COOD): δ7.30, 6.85, 4.60-4.00, 3.95, 3.80, 3.00, 2.50, 2.20, 1.95, 1.80, 1.50, 1.30, 1.85;

MS (M+H): 370.

Example 21 (2)

1-{[6-(Cyclohexyloxy)-1,5-dimethyl-3,4-dihydro-2-naphthalenyl]methyl}-3-azetidinecarboxylic acid $^1$H-NMR (CD$_3$COOD): δ7.20, 6.79, 4.62, 4.32, 4.19, 3.80, 2.71, 2.29, 2.20, 2.17, 1.94, 1.78, 1.58, 1.40;

MS (M−H): 368.

Example 22

Methyl 1-{[6-(1H-indol-1-yl)-1-methyl-3,4-dihydronaphthalen-2-yl]methyl}azetidine-3-carboxylate To a solution (1 mL) of a mixture of the compound (89 mg) prepared in Example 12, indole (60 mg), cesium carbonate (194 mg) and 4,5-bis(diphenylphosphino)-9,9-dimethylxanthene (37 mg) in 1,4-dioxane, argon was blown for 5 minutes, and the mixture was treated with tris(dibenzylideneacetone)dipalladium (0) (19 mg), was filled with argon, and thereafter, was stirred at 100° C. for 1 day. Thereafter, the reaction liquid was cooled to room temperature, and was filtrated, and the obtained filtrate was purified by silica gel column chromatography (0.5-2% methanol/ethyl acetate). The obtained residue was replaced with a solution in ethyl acetate/heptane to give the title compound (34 mg). The obtained compound was used in the next reaction without purification.

Example 23

1-{[6-(1H-Indol-1-yl)-1-methyl-3,4-dihydro-2-naphthalenyl]methyl}-3-azetidinecarboxylic acid A procedure for a purpose similar to that for Example 7 was carried out by using the compound (33 mg) prepared in Example 22 to give the title compound (22 mg) having the following physical properties.

$^1$H-NMR (CD$_3$ COOD): δ7.64-7.56, 7.46-7.43, 7.38, 7.20, 7.12, 6.66, 4.66-4.12, 3.84, 2.87, 2.41, 2.31;

(LC-MS/ELSD): (Retention time: 14.65 minutes, Condition B).

Example 24

Mixture of
6-bromo-7-methoxy-1,2,3,4-tetrahydronaphthalene
and
5-bromo-6-methoxy-1,2,3,4-tetrahydronaphthalene A mixed solution of 6-methoxy-1,2,3,4-tetrahydronaphthalene (10 g) and tetrabutylammonium tribromide (29.7 g) in methylene chloride (250 mL) and methanol (150 mL) was stirred for 1.5 hours at room temperature. Thereafter, the reaction solution was diluted with MTBE and was washed sequentially with water and saturated saline. The organic layer was dried over sodium sulfate and was filtrated, and the obtained filtrate was concentrated under a reduced pressure, and thereafter, the solution was replaced with heptane to give the title compound (14.7 g). The obtained compound was used in the next reaction without purification.

Example 25

Mixture of
6-fluoro-7-methoxy-1,2,3,4-tetrahydronaphthalene
and
5-fluoro-6-methoxy-1,2,3,4-tetrahydronaphthalene Under a nitrogen atmosphere, to a solution of the compound (6.85 g) prepared in Example 24 in THF, a solution (12.5 mL) of 2.5 M n-butyllithium in hexane was added dropwise at −78° C., and the mixture was stirred at −78° C. for 15 minutes. The reaction solution was treated with a solution (30 mL) of N-fluorobenzenesulfonamide (9.84 g) in THF, and thereafter, the mixture was stirred at −78° C. for 30 minutes. Thereafter, the mixture was carefully treated with water (20 mL), and the obtained mixture was returned to room temperature. The mixture was extracted with ethyl acetate, and the organic layer was dried over sodium sulfate, and thereafter, the obtained solution was concentrated under a reduced pressure. The obtained residue was purified by using silica gel column chromatography (10-50% methylene chloride/hexane) to give the title compound (3.98 mg). The obtained compound was used in the next reaction without further purification.

Example 26

7-Fluoro-6-methoxy-3,4-dihydronaphthalen-1(2H)-one and 5-fluoro-6-methoxy-3,4-dihydronaphthalen-1(2H)-one To a mixture of the compound (3.97 g) prepared in Example 25 and glacial acetic acid (36 mL), a solution of chromium trioxide (5.06 g) in glacial acetic acid (36 mL) and water (18 mL) were added dropwise at 0° C., and the obtained mixture was returned to room temperature for over 15 minutes. Thereafter, the reaction solution was concentrated under a reduced pressure, and the obtained mixture was poured to ethyl acetate, and the mixture was washed sequentially with water and saturated sodium bicarbonate aqueous solution. The organic layer was dried over sodium sulfate, and the obtained solution was concentrated under a reduced pressure, and the obtained residue was purified by using silica gel column chromatography (0-20% ethyl acetate/hexane) to give 7-fluoro-6-methoxy-3,4-dihydronaphthalen-1(2H)-one (1.11 g). The remaining fraction was concentrated under a reduced pressure, and the obtained residue was purified by using silica gel column chromatography (methylene chloride) to give 5-fluoro-6-methoxy-3,4-dihydronaphthalen-1(2H)-one (851 mg). The physical properties of each of the title compounds were as follows.
7-Fluoro-6-methoxy-3,4-dihydronaphthalen-1(2H)-one;
$^1$H-NMR (CDCl$_3$): δ7.72, 6.75, 3.94, 2.91, 2.60, 2.13.
5-Fluoro-6-methoxy-3,4-dihydronaphthalen-1(2H)-one;
$^1$H-NMR (CDCl$_3$): δ7.86, 6.92, 3.95, 2.96, 2.61, 2.13.

Example 27

8-Fluoro-7-methoxy-4-methyl-1,2-dihydronaphthalene

To a solution of 5-fluoro-6-methoxy-3,4-dihydronaphthalen-1(2H)-one (839 mg) prepared in Example 26 in THF, a solution of 3.0 M methylmagnesium bromide in diethyl ether (1.44 mL) was added dropwise at 0° C., and the obtained mixture was stirred at 0° C. for 30 minutes, and thereafter, was returned to room temperature for over 1 hour. The reaction solution was further treated with a solution of 3.0 M methylmagnesium bromide in diethyl ether (1.44 mL), and the mixture was stirred at room temperature for 2 hours. Thereafter, the reaction solution was treated with ethyl acetate and silica, the obtained mixture was concentrated under a reduced pressure, and the obtained residue was purified by using silica gel column chromatography (0-30% ethyl acetate/hexane) to give the title compound (496 mg) having the following physical properties.
$^1$H-NMR (CDCl$_3$): δ 7.94, 6.76, 5.76, 3.88, 2.80, 2.25-2.21, 2.02.

Example 28

5-Fluoro-6-methoxy-1-methyl-3,4-dihydronaphthalene-2-carbaldehyde

To a solution (4 mL) of the compound (493 mg) prepared in Example 27 in DMF, phosphorus oxychloride (1.28 g) was added dropwise at 0° C., and the obtained mixture was stirred at 70° C. for 40 minutes. Thereafter, the reaction solution was poured to ice, and was left to stand for 30 minutes. The obtained mixture was extracted with ethyl acetate, and the organic layer was washed sequentially with water and 5% lithium chloride solution. The aqueous layer was extracted with ethyl acetate, and the organic layer was dried over sodium sulfate, and the obtained solution was concentrated under a reduced pressure. The aqueous layer was left to stand overnight, and thereafter, was extracted with ethyl acetate and the organic layer was dried over sodium sulfate. The obtained solution was mixed with the residue of each of the above-described layers and was concentrated under a reduced pressure. The obtained residue was purified by using silica gel column chromatography (0-30% ethyl acetate/hexane) to give the title compound (270 mg) having the following physical properties.
$^1$H-NMR (CDCl$_3$): δ 10.33, 7.31, 6.86, 3.93, 2.79, 2.52-2.48.

Example 29

5-Fluoro-6-hydroxy-1-methyl-3,4-dihydronaphthalene-2-carbaldehyde

A procedure for a purpose similar to that for Example 19 was carried out by using the compound (267 mg) prepared in Example 28 to give the title compound (241 mg) having the following physical properties. The obtained compound was used in the next reaction without purification.

Example 30

6-(Cyclohexyloxy)-5-fluoro-1-methyl-3,4-dihydronaphthalene-2-carbaldehyde

A procedure for a purpose similar to that for Example 8 was carried out by using the compound (100 mg) prepared in Example 29 and cyclohexanol (102 mg) to give the title compound (39 mg) having the following physical properties.
$^1$H-NMR (CDCl$_3$): δ 10.33, 7.25, 6.87, 4.32, 2.78, 2.51-2.49, 2.00, 1.83, 1.63-1.57, 1.41-1.32.

Example 31

1-{[6-(Cyclohexyloxy)-5-fluoro-1-methyl-3,4-dihydro-2-naphthalenyl]methyl}-3-azetidinecarboxylic acid A solution (100 mL) of the compound (38 mg) prepared in Example 30, azetidine-3-carboxylic acid (27 mg) and sodium cyanoborohydride (17 mg) in methanol was allowed to react at 60° C. for 45 minutes. Thereafter, the reaction solution was concentrated under a reduced pressure, and the obtained residue was purified by using silica gel column chromatography (methylene chloride:methanol:concentrated aqueous ammonia=80:18:2), and thereafter, was lyophilized by using acetonitrile/water to give the title compound (36 mg) having the following physical properties.
$^1$H-NMR (CD$_3$COOD): δ7.11, 6.90, 4.63-4.20, 3.81, 2.77, 2.32, 2.21, 1.99-1.91, 1.84-1.80, 1.61-1.55, 1.43-1.40;
(LC-MS/ELSD): (Retention time: 15.00 minutes, Condition B).

Example 31 (1)

1-{[6-(Cyclohexyloxy)-7-fluoro-1-methyl-3,4-dihydro-2-naphthalenyl]methyl}-3-azetidinecarboxylic acid A procedure for a purpose similar to that for Example 31 was carried out by using 7-fluoro-6-methoxy-3,4-dihydronaphthalen-1(2H)-one (1.10 g) prepared in Example 26, cyclohexanol (154 mg) and azetidine-3-carboxylic acid (18 mg) to give the title compound (31 mg) having the following physical properties.

$^1$H-NMR (CD$_3$COOD): δ7.13, 6.87, 4.67-4.19, 3.81, 2.69, 2.32, 2.19, 1.98-1.95, 1.80, 1.60-1.53, 1.43-1.38;

(LC-MS/ELSD): (Retention time: 14.96 minutes, Condition B).

Example 32

6-Formyl-5-methyl-7,8-dihydronaphthalen-2-yl trifluoromethanesulfonate

To a solution of the compound (3.0 g) prepared in Example 4 in dichloromethane (30 mL), DIPEA (3.2 mL) and N,N-bis(trifluoromethylsulfonyl)aniline (6.3 g) were added, and the mixture was stirred at room temperature for 4 hours. The mixture was extracted by adding water and dichloromethane, and the organic layer was washed with saturated saline, and thereafter, was dried over sodium sulfate. After concentration under a reduced pressure, the product was purified by silica gel column chromatography (hexane:ethyl acetate=100:0 to 85:15) to give the title compound (4.82 g) having the following physical properties.

$^1$H-NMR (CDCl$_3$): δ10.37, 7.60, 7.19, 7.13, 2.80, 2.59-2.51.

Example 33

6-(1,3-Dioxolan-2-yl)-5-methyl-7,8-dihydronaphthalen-2-yl] trifluoromethanesulfonate To a solution of the compound (2.78 g) prepared in Example 32 in toluene (30 mL), ethylene glycol (2.42 mL) and p-toluenesulfonic acid monohydrate (83 mg) were added, and the mixture was heated under stirring at 130° C. for 5 hours. To the mixture, 1 N sodium hydroxide (45 mL) was added, and the mixture was extracted with ethyl acetate. The organic layer was washed with saturated saline and was dried over sodium sulfate. After concentration under a reduced pressure, the residue was purified by aminosilica gel column chromatography (hexane:ethyl acetate=100:0 to 85:15) to give the title compound (2.52 g) having the following physical properties.

$^1$H-NMR (CDCl$_3$): δ7.35, 7.10, 7.04, 5.82, 4.13-3.96, 2.77, 2.32, 2.14.

Example 34

2-[6-(Cyclohexylmethyl)-1-methyl-3,4-dihydronaphthalen-2-yl]-1,3-dioxolane

The compound (230 mg) prepared in Example 33 was dissolved in THF (3 mL) and N-methylpyrrolidone (NMP) (0.6 mL), and to the mixture, tris(2,4-pentanedionato)iron (III) (Fe(acac)$_3$) (45 mg) and cyclohexylmethylmagnesium bromide (0.5 M solution in THF, 1.5 mL) were added, and the mixture was stirred at room temperature. After 30 minutes, cyclohexylmethylmagnesium bromide (0.5 M solution in THF, 1.5 mL) was added again, and the mixture was stirred at room temperature. After 2 hours, Fe(acac)$_3$ (22 mg) and cyclohexylmethylmagnesium bromide (0.5 M solution in THF, 1.5 mL) were added to the mixture, and the mixture was further stirred at room temperature for 1 hour. To the mixture, saturated ammonium chloride aqueous solution was added, the mixture was extracted with ethyl acetate, the organic layer was washed with saturated saline and was dried over sodium sulfate. After concentration under a reduced pressure, the product was purified by silica gel column chromatography (hexane:ethyl acetate=100:0 to 90:10) to give the title compound (155 mg) having the following physical properties.

$^1$H-NMR (CDCl$_3$): δ7.46, 7.23, 6.99, 5.85, 4.15-3.94, 2.73, 2.56-2.43, 2.29, 2.14, 1.74-1.47, 1.25-1.11, 1.04-0.84.

Example 35

Methyl 1-{[6-(cyclohexylmethyl)-1-methyl-3,4-dihydronaphthalen-2-yl]methyl}azetidine-3-carboxylate A procedure for a purpose similar to that for Example 20 was carried out by using the compound (155 mg) prepared in Example 34 and methyl azetidine-3-carboxylate hydrochloride (83 mg) to give the title compound (104 mg) having the following physical properties.

$^1$H-NMR (CDCl$_3$): δ7.19, 6.98, 6.90, 3.71, 3.58-3.51, 3.40-3.25, 2.69, 2.44, 2.28, 2.11, 1.74-1.60, 1.57-1.42, 1.24-1.10, 1.02-0.85.

Example 36

1-{[6-(Cyclohexylmethyl)-1-methyl-3,4-dihydro-2-naphthalenyl]methyl}-3-azetidinecarboxylic acid

[Chemical Formula 24]

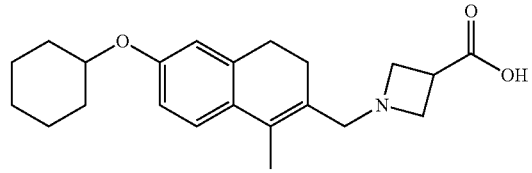

A procedure for a purpose similar to that for Example 7 was carried out by using the compound (100 mg) prepared in Example 35 to give the title compound (77 mg) having the following physical properties.

$^1$H-NMR (CD$_3$OD): δ7.29, 7.00, 6.94, 4.29-4.12, 3.52-3.30, 2.73, 2.44, 2.33-2.22, 1.79-1.44, 1.32-1.13, 1.05-0.83; MS (M−H): 353.

Biological Experimental Examples will be described hereinbelow, and the effects of the compound of the present invention were confirmed based on the experimental methods.

Biological Experimental Example 1

Measurement of the Inhibitory Action of the Compound of the Present Invention on Binding of [$^{33}$P]-S1P to S1P$_5$ (EDG-8)

A reaction was carried out in a 96-well microplate by using membrane fractions of Chinese hamster ovary (CHO) cells each of which was made to overexpress human S1P$_1$ (EDG-1) or human S1P$_5$ gene respectively, in an amount of the membrane fraction of 1 mg protein/mL. To each of the wells, 100 μL of a vehicle (DMSO) solution or a ligand solution at a two-fold concentration diluted with Binding Buffer (50 mmol/L, Tris pH 7.5, 5 mmol/L, MgCl$_2$, 0.5% BSA and Complete EDTA free (1 tablet/50 mL)) and 504 of 0.16 nmol/L [$^{33}$P]-S1P (manufactured by American Radio-labeled Chemicals, Inc.) diluted with Binding Buffer were added, and thereafter, each of membrane fraction solutions (50 μL) was added and the reaction was carried out at room temperature for 60 minutes. After the reaction, suction filtration was carried out by using a 96-well UNIFILTER, and the 96-well microplate was washed with Wash Buffer (50 mmol/L, Tris pH 7.5, 0.5% BSA) (150 mL), and thereafter, was dried at 60° C. for 45 minutes. MicroScint (trade name) 20 (50 μL/well) was added and the plate was covered with TopSeal-A, and thereafter, the radioactivity was measured by using TopCount (manufactured by PerkinElmer Inc.).

[Results]

The compound of the present invention exhibited the inhibitory activity (IC50 value) as shown in the following table on binding of [$^{33}$P]-S1P to $S1P_1$ or $S1P_5$. In addition, as Comparative Compound A, 1-{[6-(4-butylphenoxy)-1-methyl-3,4-dihydronaphthalen-2-yl]methyl}azetidine-3-carboxylic acid hydrochloride described in Example 31 (69) of Patent Literature 1 was used. As a result, it was found that while Comparative Compound A had both $S1P_1$ and $S1P_5$ receptor agonist activities, all the compounds of the present invention improved the balance of an $S1P_5$ receptor agonist activity against an $S1P_1$ receptor agonist activity.

TABLE 1

| Compound | Binding Activity $IC_{50}$ (nM) | |
| --- | --- | --- |
|  | $S1P_1$ | $S1P_5$ |
| Comparative Compound A | 475 | 76 |
| Example 9 (2) | >10000 | 57.2 |
| Example 21 | >10000 | 16 |
| Example 14 (3) | >10000 | 67.2 |
| Example 14 (1) | >10000 | 22.4 |

Biological Example 2

Evaluation of S1P Receptor Agonist Activities of the Compound of the Present Invention by Monitoring the Concentration of Produced Intracellular Cyclic AMP CHO cells which were made to overexpress either human $S1P_1$ (EDG-1) or human $S1P_5$ (EDG-8) gene respectively were cultured in Ham's F12 Medium (manufactured by Gibco-BRL) containing 10% FBS (fetal bovine serum), penicillin/streptomycin and geneticin (0.25 mg/mL). The medium was removed from the cultured cells, the cultured cells were washed once with phosphate-buffered saline, and the cultured cells were treated with a vehicle (DMSO) solution or a compound solution each of which was diluted with Buffer (Hanks' balanced salt solution containing 20 mmol/L HEPES, 0.1 or 0.2% BSA, 1 mmol/L IBMX and 50 μmol/L forskolin) at 37° C. for 30 minutes. Thereafter, the cultured cells were washed once with phosphate-buffered saline. After lysing the cells, the concentration of cyclic AMP in the cell lysate were measured by using cAMP Assay Kit (GE Healthcare).

[Results]

As a result, it was found that the compound of the present invention had a selective $S1P_5$ receptor agonist activity against $S1P_1$ receptor. For example, the compound prepared in Example 21 had an EC 50 value with regard to $S1P_1$ receptor of 9991.8 nM, while the compound prepared in Example 21 had an EC 50 value with regard to $S1P_5$ receptor of 0.2 nM.

Preparation Examples

Preparation Example 1

The following components were mixed in a conventional manner and compressed to give 10,000 tablets each containing 10 mg of the active component.

| | |
| --- | --- |
| 1-{[6-(Cyclohexyloxy)-3-methyl-3,4-dihydro-2-naphthalenyl]methyl}-3-azetidinecarboxylic acid | 100 g |
| Carboxymethyl cellulose calcium (a disintegrating agent) | 20 g |
| Magnesium stearate (a lubricant) | 10 g |
| Microcrystalline cellulose | 870 g |

Preparation Example 2

The following components were mixed in a conventional manner. Thereafter, the mixture was filtered through a dust filter, and 5 ml aliquots were charged into ampules. The ampules were heat sterilized by an autoclave to give 10,000 ampules each containing 20 mg of the active component.

| | |
| --- | --- |
| 1-{[6-(Cyclohexyloxy)-3-methyl-3,4-dihydro-2-naphthalenyl]methyl}-3-azetidinecarboxylic acid | 200 g |
| Mannitol | 20 g |
| Distilled water | 50 L |

INDUSTRIAL APPLICABILITY

The compound of the present invention has a selective $S1P_5$ receptor agonist activity, and therefore, is useful for treating $S1P_5$-mediated disease, for example, neurodegenerative disease and the like.

The invention claimed is:
1. A compound of the following general formula (I):

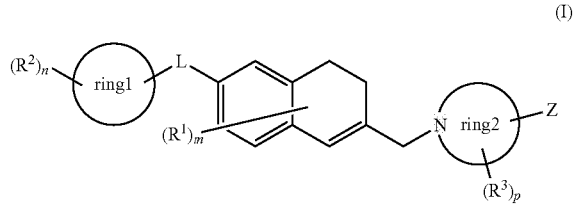

wherein, $R^1$ represents a C1-4 alkyl group or a halogen atom;
$R^2$ represents a C1-3 alkyl group, a halogen atom or a C1-3 haloalkyl group;
$R^3$ represents a C1-4 alkyl group;
L represents a bond, —$CH_2$— or —O—;
Z represents a carboxyl group which may be substituted with a C1-8 alkyl group;
ring 1 represents (1) cyclopentane, (2) cyclohexane, (3) cycloheptane, (4) cyclopentene, (5) benzene, (6) pyridine, (7) naphthalene, (8) indole, or (9) dihydroindole;
ring 2 represents (1) azetidine or (2) pyrrolidine;
m represents an integer of 0 to 2;

n represents an integer of 0 or 1;
p represents an integer of 0 or 1; and
when m is 2, a plurality $R^1$s may be the same or different,
with proviso that when L is —O— and ring 1 is benzene, $R^2$ represents a halogen atom or trifluoromethyl group,
a salt thereof, a solvate thereof, an N-oxide thereof, or a prodrug thereof.

2. The compound, a salt thereof, a solvate thereof, an N-oxide thereof, or a prodrug thereof according to claim 1, wherein m is an integer of 1 or 2.

3. The compound, a salt thereof, a solvate thereof, an N-oxide thereof, or a prodrug thereof according to claim 1, wherein the compound is (1) 1-{[6-(cyclohexyloxy)-3,4-dihydro-2-naphthalenyl]methyl}-3-azetidinecarboxylic acid, (2) 1-{[6-(cyclohexyloxy)-3-methyl-3,4-dihydro-2-naphthalenyl]methyl}-3-azetidinecarboxylic acid, (3) 1-{[1-methyl-6-(2-pyridinyl)-3,4-dihydro-2-naphthalenyl]methyl}-3-azetidinecarboxylic acid, (4) 1-[(1-methyl-6-phenyl-3,4-dihydro-2-naphthalenyl)methyl]-3-azetidinecarboxylic acid, or (5) 1-{[6-(4-fluorophenoxy)-1-methyl-3,4-dihydro-2-naphthalenyl]methyl}-3-azetidinecarboxylic acid.

4. A pharmaceutical composition comprising the compound of general formula (I), a salt thereof, a solvate thereof, an N-oxide thereof, or a prodrug thereof according to claim 1.

5. The pharmaceutical composition according to claim 4, which is an $S1P_5$ agonist.

6. The pharmaceutical composition according to claim 4, which is an agent for preventing and/or treating an S1P5-mediated disease.

7. The pharmaceutical composition according to claim 6, wherein the $S1P_5$-mediated disease is neurodegenerative disease, autoimmune disease, infection or cancer.

8. The pharmaceutical composition according to claim 7, wherein the neurodegenerative disease is schizophrenia, Binswanger's disease, multiple sclerosis, neuromyelitis optica, Alzheimer's disease, cognitive impairment, amyotrophic lateral sclerosis or spinocerebellar degeneration.

9. A method for treating an $S1P_5$-mediated disease, comprising administering to a mammal an effective amount of a compound of the following general formula (I):

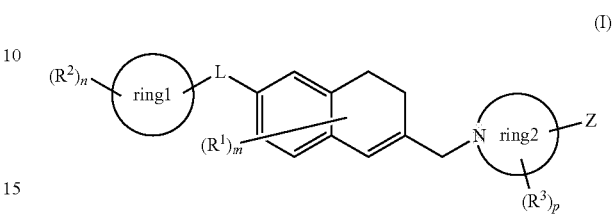

wherein, $R^1$ represents a C1-4 alkyl group, or a halogen atom;
$R^2$ represents a C1-3 alkyl group, a halogen atom or a C1-3 haloalkyl group;
$R^3$ represents a C1-4 alkyl group;
L represents a bond, —$CH_2$— or —O—,
Z represents a carboxyl group which may be substituted with a C1-8 alkyl group;
ring 1 represents (1) cyclopentane, (2) cyclohexane, (3) cycloheptane, (4) cyclopentene, (5) benzene, (6) pyridine, (7) naphthalene, (8) indole, or (9) dihydroindole;
ring 2 represents (1) azetidine or (2) pyrrolidine;
m represents an integer of 0 to 2;
n represents an integer of 0 or 1;
p represents an integer of 0 or 1; and
when m is 2, a plurality $R^1$s may be the same or different;
a salt thereof, a solvate thereof, an N-oxide thereof, or a prodrug thereof.

* * * * *

UNITED STATES PATENT AND TRADEMARK OFFICE
CERTIFICATE OF CORRECTION

| | |
|---|---|
| PATENT NO. | : 11,471,436 B2 |
| APPLICATION NO. | : 15/532389 |
| DATED | : October 18, 2022 |
| INVENTOR(S) | : Kensuke Kusumi et al. |

It is certified that error appears in the above-identified patent and that said Letters Patent is hereby corrected as shown below:

On the Title Page

Item (56) Other Publications, Column 2, Line 11, delete "Suppliementary" and insert --Supplementary-- therefor;

Item (57) Abstract, Column 2, Line 3, delete "S1P5" and insert --S1P$_5$-- therefor;

Item (57) Abstract, Column 2, Line 7, delete "S1P5-mediated" and insert --S1P$_5$-mediated-- therefor;

In the Claims

In Claim 1, Column 43, Line 3, after "plurality", insert --of--;

In Claim 6, Column 43, Line 30, after "for", delete "preventing and/or";

In Claim 6, Column 43, Lines 30-31, delete "S1P5-mediated" and insert --S1P$_5$-mediated-- therefor;

In Claim 9, Column 44, Line 23, delete "–O–," and insert -- –O–;-- therefor; and In Claim 9, Column 44, Line 33, after "plurality", insert --of--.

Signed and Sealed this
Tenth Day of January, 2023

*Katherine Kelly Vidal*

Katherine Kelly Vidal
*Director of the United States Patent and Trademark Office*